(12) United States Patent
Oku et al.

(10) Patent No.: US 8,153,759 B2
(45) Date of Patent: Apr. 10, 2012

(54) DEPSIPEPTIDE CONTAINING LACTIC ACID RESIDUE

(75) Inventors: Hiroyuki Oku, Kiryu (JP); Yuya Shimoda, Kiryu (JP); Aya Inoue, Kiryu (JP); Chie Takayama, Kiryu (JP); Keiichi Yamada, Kiryu (JP); Ryoichi Katakai, Kiryu (JP)

(73) Assignee: National University Corporation Gunma University, Gunma (JP)

( * ) Notice: Subject to any disclaimer, the term of this patent is extended or adjusted under 35 U.S.C. 154(b) by 327 days.

(21) Appl. No.: 12/438,694

(22) PCT Filed: Aug. 10, 2007

(86) PCT No.: PCT/JP2007/065720
§ 371 (c)(1),
(2), (4) Date: Mar. 6, 2009

(87) PCT Pub. No.: WO2008/023582
PCT Pub. Date: Feb. 28, 2008

(65) Prior Publication Data
US 2010/0099846 A1 Apr. 22, 2010

(30) Foreign Application Priority Data
Aug. 24, 2006 (JP) .................................. 2006-228281

(51) Int. Cl.
*A61K 38/00* (2006.01)
*A61K 38/12* (2006.01)
*C07K 5/00* (2006.01)
*C07K 7/00* (2006.01)
*C07K 16/00* (2006.01)
*C07K 17/00* (2006.01)

(52) U.S. Cl. ........................................ 530/323; 530/321

(58) Field of Classification Search ........................ None
See application file for complete search history.

(56) References Cited

U.S. PATENT DOCUMENTS

| 3,832,337 | A | * | 8/1974 | Ondetti et al. | .................. | 530/327 |
| 6,734,165 | B2 | * | 5/2004 | Chiosis et al. | .................. | 514/2.6 |
| 6,953,861 | B2 | * | 10/2005 | Chiosis et al. | .................. | 548/530 |
| 7,078,380 | B2 | * | 7/2006 | Cooper et al. | .................. | 514/2.4 |

FOREIGN PATENT DOCUMENTS

| JP | 2004-269462 | 9/2004 |
| WO | WO 2006/043644 | 4/2006 |

OTHER PUBLICATIONS

Shimoda, et al. "Nyusan Zanki o Fukunda Ondo Otosei Poly Depsipeptide no Gosei to Seishitsu," *Polymer Preprints*, Japan, vol. 55, No. 2 Disk, p. 4879, Sep. 5, 2006.
Oku, et al. "Ondo Otosei Poly Depsipeptide no Gosei to Seishitsu," *Polymer Preprints*, Japan, vol. 55, No. 1 Disk 1, p. 1827, May 10, 2006.
Oku, et al. "Ondo Otosei Poly Depsipeptide no Gosei to Seishitsu," *CSJ: The Chemical Society of Japan Koen Yokoshu*, vol. 85th, No. 2, p. 1216, 3 F1-50, 2005.
Suda, et al. "Poly Depsipeptide no Gosei Oyobi Seitai Zairyo eno Oyo," *Polymer Preprints*, Japan, vol. 54, No. 1 Disk 1, p. 329, 2005.
Shichiri, et al. "Synthesis and Properties of a Thermo-Responsible Plydepsipeptide Containing Hmb (2-Hydroxy-3-Methylbutanoic Acid) Residues," *Peptide Science*, vol. 2004, 41$^{st}$, pp. 633-636, 2005.
Taira, et al. "Synthesis and Properties of an Elastin Model Depsipeptide Model Depsipeptide Sequences, Containing -Gly-Val-Gly-Hmb-Pro (Hmb=2-Hydroxy-3-Methylbutanoic Acid)," *Peptide Science*, vol. 2003, 40st, pp. 177-180, 2004.
Arad, et al. "Depsipeptide Analogues of Elastin Repeating Sequences: Conformational Analysis," *Biopolymers*, vol. 29, No. 12-13, pp. 1651-1668, 1990.
Ayres, et al. "Stimulus Responsive Behavior of Elastin-Based Side Chain Polymers," *Macromolecules*, vol. 38, No. 5, pp. 1699-1704, 2005.
International Search Report dated Oct. 23, 2007.
Yoshida, et al. "Sequential Polydepsipeptides as Biodegradable Carriers for Drug Delivery Systems," *Journal of Biomedical Materials Research*, vol. 24, pp. 1173-1184, 1990.
Shikinami, "Characteristics and Application of Poly L-Lactide as Biomaterials," *Rheumatology*, vol. 21, No. 3, pp. 267-278, 1999.
Katakai, et al. "Synthesis of Sequential Polydepsipeptides Utilizing a New Approach for the Synthesis of Depsipeptides," *Biopolymers*, vol. 73, pp. 641-644, 2004.
Oku, et al. "An N-Protected Depsipeptide Free Acid Prepared by Direct Synthesis Without Using a Terminal-C Protecting Group: tert-butoxycarbonyl-L-alanyl-L-leucyl-L-lactic acid (Boc-L-Ala-L-Leu-L-Lac-OH)," *Acta Crystallographica Section E*, E60, pp. o927-o929, 2004.

(Continued)

*Primary Examiner* — Marcela M Cordero Garcia
(74) *Attorney, Agent, or Firm* — Knobbe, Martens, Olson & Bear, LLP

(57) ABSTRACT

Disclosed are a compound represented by the general formula (I) below and a polymer compound obtained by polymerizing such a compound.

$$R_1\text{-Gly-Lac-Pro-}R_2 \qquad (I):$$

where -Gly-Lac-Pro- represents a structure represented by the following formula (II),
$R_1$ represents a hydrogen atom, or an amino acid, a polypeptide or a hydroxycarboxylic acid which are linked through an amide bond,
$R_2$ represents a hydroxyl group, or an amino acid or a polypeptide which are linked through an amide bond, or a hydroxycarboxylic acid which is linked through an ester bond.

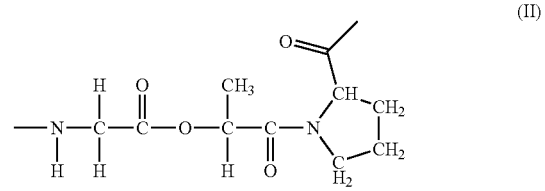

(II)

11 Claims, 8 Drawing Sheets

OTHER PUBLICATIONS

Chang, et al. "Nuclear Overhauser Effect and Computational Characterization of the β-Spiral of the Polypentapeptide of Elastin," *Journal of Biomolecular Structure & Dynamics*, vol. 6, Issue No. 5 pp. 851-858, 1989.

Urry, et al. "Nuclear Overhauser Enhancement Evidence for Inverse Temperature Dependence of Hydrophobic Side Chain Proximity in the Polytetrapeptide of Tropoelastin," *Biochemical and Biophysical Research Communications*, vol. 79, No. 3, pp. 700-706, 1977.

Urry, et al. "Two-Dimensional Proton NMR Studies on Poly(VPGVG) and its Cyclic Conformational Correlate, Cyclo(VPGVG)$_3$ ," *Biopolymers*, vol. 28, pp. 819-833, 1989.

Urry, "Free Energy Transduction in Polypeptides and Proteins Based on Inverse Temperature Transitions," *Progress in Biophysics and Molecular Biology*, vol. 57, pp. 23-57, 1992.

Urry, et al. "Temperature-Correlated Force and Structure Development in Elastomeric Polypeptides: The Ile Analog of the Polypentapeptide of Elastin," *Biopolymers*, vol. 25, pp. 1939-1953, 1986.

Rapaka, et al. "Coacervation Properties in Sequential Polypeptide Models of Elastin," *International Journal of Peptide and Protein Research*, vol. 12, pp. 81-92, 1978.

Arad, et al. "Depsipeptide Analogues of Elastin Repeating Sequences: Synthesis," *Biopolymers*, vol. 29, pp. 1633-1649, 1990.

* cited by examiner

SEQUENCE LISTING

<160> NUMBER OF SEQ ID NOS: 10

<210> SEQ ID NO 1
<211> LENGTH: 5
<212> TYPE: PRT
<213> ORGANISM: Artificial sequence
<220> FEATURE:
<223> OTHER INFORMATION: elastin-like polypeptide

<400> SEQUENCE: 1

Gly Ile Gly Ala Pro
1               5

```
<210> SEQ ID NO 2
<211> LENGTH: 5
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: Xaa=Hmb (Hmb is valic acid residue)

<400> SEQUENCE: 2

Gly Val Gly Xaa Pro
1               5

<210> SEQ ID NO 3
<211> LENGTH: 6
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: Xaa=Hmb (Hmb is valic acid residue)

<400> SEQUENCE: 3

Gly Val Gly Xaa Ala Pro
1               5

<210> SEQ ID NO 4
<211> LENGTH: 5
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: Xaa=Hmb (Hmb is valic acid residue)

<400> SEQUENCE: 4

Val Pro Gly Xaa Gly
1               5

<210> SEQ ID NO 5
<211> LENGTH: 6
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Xaa=Hmb (Hmb is valic acid residue)

<400> SEQUENCE: 5

Val Ala Pro Gly Xaa Gly
1               5

<210> SEQ ID NO 6
<211> LENGTH: 4
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: Xaa=any alpha-amino acid
```

```
<220> FEATURE:
<221> NAME/KEY: MISC_FEATURE
<222> LOCATION: (4)..(4)
<223> OTHER INFORMATION: Pro is modified with a lactic acid residue

<400> SEQUENCE: 6

Xaa Xaa Gly Pro
1

<210> SEQ ID NO 7
<211> LENGTH: 4
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: Pro is modified with a lactic acid residue

<400> SEQUENCE: 7

Gly Ile Gly Pro
1

<210> SEQ ID NO 8
<211> LENGTH: 4
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: Pro is modified with a lactic acid residue

<400> SEQUENCE: 8

Ala Ile Gly Pro
1

<210> SEQ ID NO 9
<211> LENGTH: 4
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: Pro is modified with a lactic acid residue

<400> SEQUENCE: 9

Gly Val Gly Pro
1

<210> SEQ ID NO 10
<211> LENGTH: 3
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: Pro is modified with a lactic acid residue

<400> SEQUENCE: 10

Val Gly Pro
1
```

DEPSIPEPTIDE CONTAINING LACTIC ACID RESIDUE

CROSS-REFERENCE TO RELATED APPLICATIONS

This application is the U.S. National Phase under 35 U.S.C. §371 of International Application PCT/JP2007/065720, filed Aug. 10, 2007, which was published in a non-English language, which claims priority to Japanese Patent Application No. 2006-228281, filed Aug. 24, 2006.

TECHNICAL FIELD

The present invention relates to a novel depsipeptide compound that can be used as a temperature responsive material and a depsipeptide polymer obtained by polymerizing the depsipeptide compound. More specifically, the present invention relates to a novel depsipeptide compound having, as a constituent component, a depsipeptide obtained by subjecting a lactic acid residue and an amino acid residue to a dehydration condensation, and a depsipeptide polymer obtained by polymerizing the depsipeptide compound.

The material of the present invention can be used as a temperature responsive material which aggregates or dissolves in a buffer solution or a water-containing solvent in response to temperature, and hence is useful for constituting a bioabsorbable composition, an environmental degradable composition, a cell adhesion agent, an artificial muscle, a microcapsule, a biomachine, a biosensor, a separation membrane, a test kit, and the like.

BACKGROUND ART (1) Current situation of depsipeptide and related materials:

The depsipeptide is a polymer or an oligomer in which a main chain is composed of ester bonds and amide bonds as represented in Formula (A). The skeleton of the structure is formed of amide bonds and ester bonds.

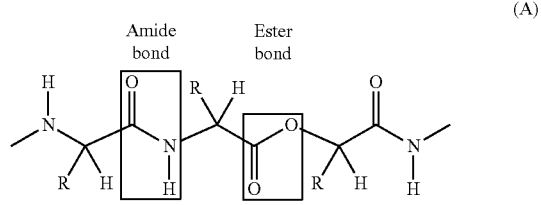

(A)

The amide bond and the ester bond contained in the skeleton have been known to have three kinds of interactions at a molecular level. That is, between amide bonds, the intramolecular and intermolecular hydrogen bonds cause a strong interaction and stabilization of the molecular structure. Accordingly, macroscopically, insolubilization to a solvent and improvement of mechanical strength are expected. In addition, between ester bonds, there is no intermolecular and intramolecular interactions by a hydrogen bond at a molecular level. Accordingly, macroscopically, flexibility or weakness due to decrease in mechanical strength is expected. That is, between the amide bond and the ester bond, a relatively weak intramolecular and intermolecular hydrogen bond between an oxygen atom in the ester site and NH in the amide site causes a structural stabilization of the molecular structure at a molecular level. Accordingly, macroscopically, a little improvement of the mechanical strength is expected as compared to the case of only amide bonds. Therefore, the depsipeptide can be used as a material having characteristics of an oligomer or a polymer formed of an amino acid and a hydroxycarboxylic acid. That is, a material having wide range of properties can be synthesized by changing the kinds, the compositions, and the sequences of the amino acids and the hydroxycarboxylic acids. Further, as advantages of the depsipeptide, the following three points are given: the depsipeptide hardly causes inflammation in a body; the depsipeptide can be used as a delivery material for a substance susceptible to an acid component; and a molded product of the depsipeptide has extremely high strength due to intermolecular or intramolecular interaction such as a hydrogen bond and a hydrophobic interaction. Thus, the depsipeptide is an extremely attractive substance.

Various studies have been actually conducted with respect to the polydepsipeptide. For example, it has been known that, when the side chain of the hydroxycarboxylic acid in the polydepsipeptide is changed to H—, $CH_3$—, $(CH_3)_2CH$—, or $(CH_3)_2CH$—$CH_2$— so that the hydrophobicity and the size of the steric hindrance are changed, the degradation rate in an organism can be adjusted within the wide range of 2 weeks to 6 months. In addition, the polydepsipeptide is characterized in that no inflammation is recognized in the joining surface with an organism tissue (Non-Patent Document 1).

There is no inflammation with the polydepsipeptide, but in general, it has been known that, when the degradation rate of a material using only polyhydroxycarboxylic acid is high, an inflammation reaction is easily caused (Non-Patent Document 2). This may be because a relatively strong acid component such as lactic acid or glycolic acid is accumulated. On the other hand, in case of polydepsipeptide, it is conceivable that the acid component is not accumulated because the polydepsipeptide produces a depsipeptide oligomer as a degradation substance, and no inflammation was found even at a high degradation rate.

The polydepsipeptide has been improved in recent years from the viewpoint of a synthesis method. For example, there are studies on reduction in the number of reaction steps. That is, it has become possible to produce a didepsipeptide by reacting, using an aminopyridine compound as a catalyst, a carboxyl group in an amino acid having a protected amino group with a hydroxyl group in a hydroxycarboxylic acid having a carboxylic group without protection (Patent Document 1 and Non-Patent Documents 3 and 4). By those studies, a depsipeptide having a repeating sequence has been successfully produced more easily without forming a protecting group of the carboxyl group in the hydroxycarboxylic acid. That is, even with a synthesis facility in a laboratory (several milliliters to several hundreds of milliliters), it has become possible to synthesize at once a pure polydepsipeptide in a unit of several hundreds of milligrams to several grams. In case where the scale is expanded to plant facilities (several liters to several hundreds of liters), the polydepsipeptide can be produced in a unit of several kilograms.

(2) Current situation of temperature responsive material:

In recent years, studies on temperature responsive materials which aggregate with the increase in the temperature have attracted attentions. The temperature responsive materials are expected to be applied to, using a property of containing much water, a drug delivery substance, a wound dressing material, an artificial muscle, a microcapsule, a biomachine, a biosensor, a separation membrane, and the like.

According to a method using a depsipeptide as well, temperature responsive materials have been developed in recent years (Patent Document 2 and Non-Patent Document 5). For example, depsipeptide polymers having repeating units of -Gly-Val-Gly-Hmb-Pro-(SEQ ID NO: 2) and -Gly-Val-Gly-Hmb-Ala-Pro-(SEQ ID NO: 3) (Hmb=valic acid residue) are disclosed. Those depsipeptide polymers are characterized by including a β-branched hydroxycarboxylic acid called valic acid (Hmb). This is because, in the position of the valic acid in the sequence represented herein, a β-branched amino acid (or hydroxycarboxylic acid) may be required for expression of the temperature responsiveness.

In the temperature responsive material formed of a depsipeptide or a peptide, it has been considered that the role of the β-branched amino acid is to cause a reversible temperature responsiveness by the following mechanism: by heating, water molecules subjected to hydrophobic hydration in Val-γ$CH_3$ (or Hmbγ$CH_3$) and Proδ$CH_2$ liberate from a side chain due to increase in molecular movement by heat energy and a hydrophobic interaction among side chains is caused (aggregation phenomenon of increased temperature responsiveness); and the reverse process is caused (dissolution phenomenon of decreased temperature responsiveness) (as examples of Val residue, Non-Patent Documents 6 to 9) (as examples of Ile residue, Non-Patent Document 10).

In the temperature responsive material formed of a peptide, it has been pointed that, in the case where an alanine residue but not the β-branched amino acid is used, the material shows an irreversible temperature responsiveness and becomes insoluble to water immediately (Non-Patent Document 11). That is, in the conventional temperature responsive material, it is necessary to introduce the β-branched amino acid into a determined position, and thus the conventional temperature responsive material has had a problem in a strict restriction in the sequence.

The hydroxycarboxylic acids that have been actually sold in the market in the past as biomaterials contain mainly lactic acid and glycolic acid as constituent components. These are excellent because there are many examples for use of the components, and advantages and disadvantages thereof are known.

On the other hand, the temperature responsive material formed of a depsipeptide up to the present uses valic acid (Hmb) as another hydroxycarboxylic acid. The valic acid is contained in many natural products as antibiotic substances, thereby being expected to have little problems. However, there are a few cases where the valic acid is used as a biomaterial. Therefore, there has been a problem in that many examinations including an examination about disposition may be necessary to apply the temperature responsive polymer containing valic acid (Hmb) to an organism.

As an interesting study, a polydepsipeptide sequence involved in the temperature responsive material was reported in 1990 (Non-Patent Documents 12 and 13). In the documents, polymers having two kinds of repeating sequences of -Val-Pro-Gly-Hmb-Gly (SEQ ID NO: 4) and -Val-Ala-Pro-Gly-Hmb-Gly- (SEQ ID NO: 5) was reported. The polymers had problems in the following four points: a temperature responsiveness was not exhibited; there were many synthesis steps; most important reaction called condensation reaction, in which an ester bond or an amide bond is produced, was a low-yield reaction (five reactions were described and respective yields were 23, 33, 54, 70, and 76%); and only 10 mg of a polymer as a final product was obtained as a result of the low yield. Actually, it is notable that the document described how difficult the synthesis of the sequence was.

That is, except for cases which the inventors of the present invention reported (Patent Document 2 and Non-Patent Document 5), up to the present, it has been generally considered that it is extremely difficult to synthesize the sequence of a polydepsipeptide and an oligodepsipeptide involved in the temperature responsive material and the synthesis is not practical.

Patent Document 1: JP 2004-269462 A
Patent Document 2: WO 2006/043644A1
Non-Patent Document 1: Yoshida et al., Journal of Biomedical Materials Research, 1990, Vol. 24, page 1173
Non-Patent Document 2: Yasuo Shikinami, Rheumatology, 1999, Vol. 21 No. 3, page 267
Non-Patent Document 3: Katagai et al., 2004, Vol. 73, page 641
Non-Patent Document 4: Oku et al., Acta Crystallographica Section E, 2004, Vol. E60, page 927,
Non-Patent Document 5: Nanasato et al., Peptide Science 2004, 2005, page 633
Non-Patent Document 6: Chan et al., Journal of Biomolecular Structure and Dynamics, 1989, Vol. 6, page 851
Non-Patent Document 7: Urry et al., Biochemistry and Biophysics Research Communication, 1977, Vol. 79, page 700
Non-Patent Document 8: Urry et al., Biopolymers, 1989, Vol. 28, page 819
Non-Patent Document 9: Urry et al., Progress in Biophysics and Molecular Biology, 1992, Vol. 57, page 23
Non-Patent Document 10: Urry et al., Biopolymers, 1986, Vol. 25, page 1939
Non-Patent Document 11: Rapaka et al., International Journal of Peptide and Protein Research, 1978, page 81
Non-Patent Document 12: Arad & Goodman, Biopolymers, 1990, Vol. 29, page 1633
Non-Patent Document 13: Arad & Goodman, Biopolymers, 1990, Vol. 29, page 1651

DISCLOSURE OF THE INVENTION

An object of the present invention is to provide a novel depsipeptide that has a favorable constituent component as a biomaterial and can be used as a temperature responsive material.

The inventors of the present invention have focused on a novel amino acid sequence in order to achieve the above object. That is, the inventors have focused on the sequence of an elastin-like polypeptide including alanine (Ala), an amino acid other than the β-branched amino acid, i.e. -Gly-Ile-Gly-Ala-Pro- (SEQ ID: NO. 1), which did not conventionally attract attention because of the irreversible temperature responsiveness and insolubility as a result of the irreversibility. Further, the inventors have planed chemical synthesis of a depsipeptide having a sequence of -$X_1$-$X_2$-Gly-Lac-Pro- ($X_1$ and $X_2$ each represent an arbitrary amino acid residue) (SEQ ID NO: 6), in which alanine (Ala) is substituted with lactic acid (Lac) as a hydroxycarboxylic acid.

First, as the polydepsipeptide having the sequence of -$X_1$-$X_2$-Gly-Lac-Pro- (SEQ ID NO: 6), the inventors have planed chemical synthesis of compounds represented by poly(Gly-Ile-Gly-Lac-Pro) (SEQ ID NO: 7) and poly(Ala-Ile-Gly-Lac-Pro) (SEQ ID NO: 8). By probing the synthesis method and conditions in each reaction stage, the compounds have been chemically produced successfully in a unit or several hundreds of milligrams to several grams with one step irrespective of laboratory-scale facilities (several milliliters to several hundreds of milliliters).

Further, these polydepsipeptides have easily become aqueous solutions, and clear temperature responsiveness has been confirmed by visual observation or with a measurement device. In addition, the behavior of the temperature responsiveness has been confirmed to be reversible. Thus, various depsipeptides containing lactic acid residues have been synthesized and the temperature responsiveness thereof has been extensively studied, thereby, the present invention has been completed.

That is, the present invention is as follows.

[1] A compound, which is represented by the following general formula (I)

R$_1$-Gly-Lac-Pro-R$_2$ (I):

where -Gly-Lac-Pro- represents a structure represented by the following formula (II), R$_1$ represents a hydrogen atom, or an amino acid, a polypeptide or a hydroxycarboxylic acid which are linked through an amide bond, R$_2$ represents a hydroxyl group, or an amino acid or a polypeptide which are linked through an amide bond, or a hydroxycarboxylic acid which is linked through an ester bond.

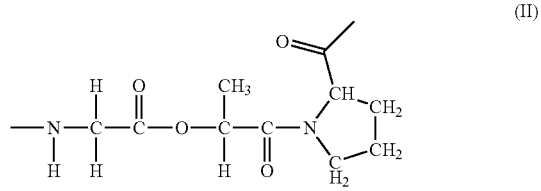

(II)

[2] The compound according to [1], wherein the general formula (I) is X$_1$-X$_2$-Gly-Lac-Pro (SEQ ID NO: 6) where X$_1$ and X$_2$ represent an α-amino acid residue.

[3] A polymer, which is obtained by polymerizing the compound according to [1] or [2].

[4] The compound according to [1] or [2], or the polymer according to claim 3, wherein a sugar chain sequence, a protein, a polysaccharide, a metal complex, a polymer carrier, a gel, a film, a latex particle, a metal fine particle, an inorganic fine particle, a glass plate, or a plastic plate is linked to a terminal.

[5] A composition, which is obtained by mixing the compound according to [1] or [2] or the polymer according to [3] with water, a buffer solution, a salt solution, or a water-containing organic solvent, and forms a solvation state, a gel state, a suspension, a uniform solution, or a phase separation state.

[6] The composition according to [5], which releases water molecules by heating and incorporates water molecules by cooling.

[7] A temperature responsive composition, comprising the compound according to [1] or [2] or the polymer according to [3].

Figure 11:
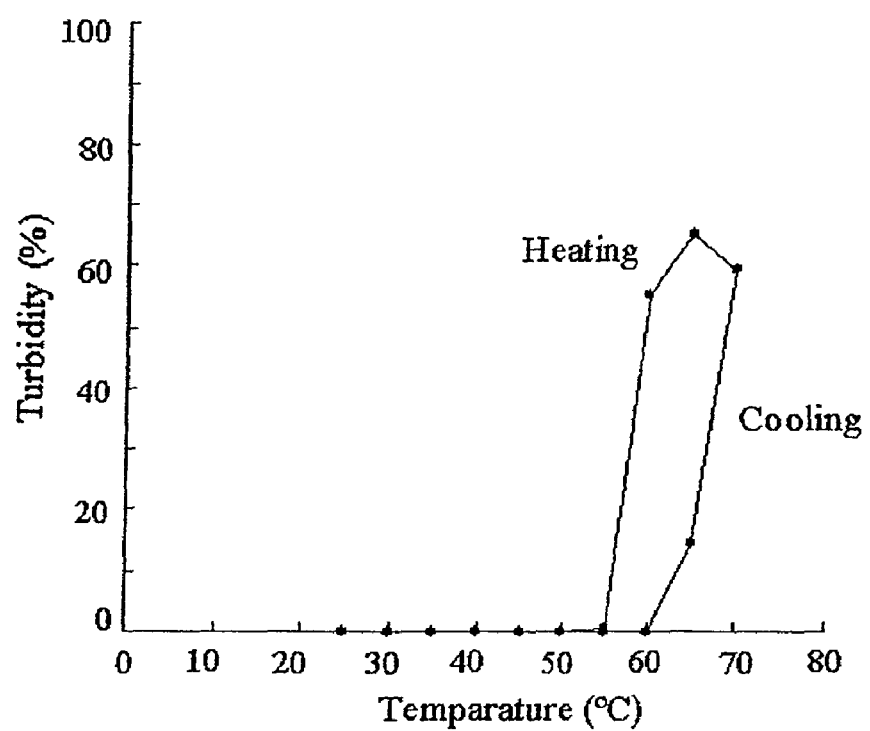

FIG. 11 illustrates a graph obtained by the following procedure: an aqueous solution of poly(Gly-Val-Gly-Lac-Pro) (SEQ ID NO: 9) (40 mg/mL) which is one embodiment of the present invention was put in a 1-mm-thick quartz cell for absorption spectra; the temperature was increased at a rate of 1° C./5 minutes between 20° C. and 70° C. and then decreased; transmittance (%) was measured with respect to a light of 350 nm at each temperature in a 1° C. interval; and a turbidity (%) obtained by subtracting the transmittance (%) from 100 was plotted.

DESCRIPTION OF THE PREFERRED EMBODIMENTS

The compound (depsipeptide) of the present invention is represented by the following general formula (I).

$R_1$-Gly-Lac-Pro-$R_2$      (I)

In the formula (I), -Gly-Lac-Pro- represents a tridepsipeptide structure represented by the following formula (II) in which a glycine residue, a lactic acid residue, and a proline residue are linked.

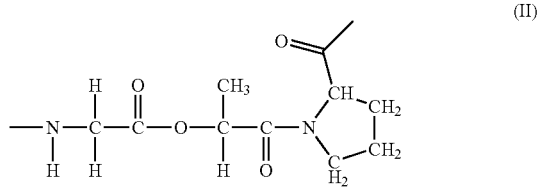

(II)

In addition, $R_1$ represents an H atom in the amino group, an amino acid, a polypeptide, or a hydroxycarboxylic acid which is linked through an amide bond, and $R_2$ represents an OH group in the carboxylic acid, an amino acid or a polypeptide which is linked through an amide bond, or a hydroxycarboxylic acid which is linked through an ester bond.

If $R_1$ represents an amino acid or a polypeptide, the amino terminal of $R_1$ may be added with a protecting group of the amino group. In addition, if $R_2$ represents an OH group, or an amino acid, or a polypeptide, the carboxy terminal of $R_2$ may be added with a protecting group of the carboxyl group. As the protecting group of the amino group, Boc (tert-butoxycarbonyl: (t-Bu-O—CO—)) and the like are exemplified. As the protecting group of the carboxyl group, OSu (N-hydroxysuccine imide), OBzl (benzyl: (—O—$CH_2$—$C_6H_5$)), or the like is exemplified.

The amino acid (including amino acids constituting polypeptides) as $R_1$ and $R_2$ is preferably an α-amino acid. In addition, an amino acid may have a modified side chain or have a peptide linked to the side chain. In addition, when $R_1$ and $R_2$ each represent a polypeptide, the number of the amino acids is preferably 2 to 20 and more preferably 2 to 9.

The kind of amino acids (including amino acids constituting polypeptides) as $R_1$ and $R_2$ is selected in order to adjust the responsive temperature, solubility, and swelling property according to the components of the temperature responsive composition. For example, in general, when the amino acid does not have electric charge, with a larger hydrophobicity of the side chain in the amino acid, the responsive temperature can be adjusted toward a lower temperature side, and with a larger hydrophilicity, the responsive temperature can be adjusted toward a higher temperature side. The fact is obvious from the related studies by the inventors of the present invention (for example, Macromolecules, 1998, Vol. 31, page 3383; Macromolecules, 1996, Vol. 29, page 1065) or research example of Urry et al. (JP 2004-501784 A).

In addition, examples of hydroxycarboxylic acid as $R_1$ and $R_2$ include valic acid, lactic acid, and glycolic acid.

In the compound of the present invention, the sequence represented by the general formula (I) is preferably $X_1$-$X_2$-Gly-Lac-Pro (SEQ ID NO: 6). Here, $X_1$ and $X_2$ each represent an arbitrary α-amino acid residue.

Specific examples thereof include, but are not limited to, Ala-Ile-Gly-Lac-Pro (SEQ ID NO: 8), Gly-Ile-Gly-Lac-Pro (SEQ ID NO: 7), and Gly-Val-Gly-Lac-Pro (SEQ ID NO: 9).

The polymer compound of the present invention is a polymer obtainable by polymerizing the depsipeptide compound represented by the general formula (I).

The structure of the polymer compound is preferably a linear structure, and may have a branched chain which is branched from a side chain in the amino acid.

The polymerization degree of the depsipeptide is not particularly limited and may be an oligomer having about 2 to 10 repeated depsipeptide compounds. The total number of the amino acid residues and hydroxylic acid residues contained in the polymer compound of the present invention is preferably 1,000 or less and more preferably 500 or less. The polymer compound of the present invention has a molecular weight of preferably 1,500 to 100,000 and more preferably 1,500 to 50,000.

The polymer compound of the present invention may contain two or more kinds of depsipeptide units represented by the general formula (I).

The polymer compound of the present invention is obtained by, for example, first synthesizing the compound (depsipeptide) represented by the general formula (I) and polymerizing those compounds.

The compound represented by the general formula (I) can be obtained by a chemical synthesis as described in Examples below. With the chemical synthesis method described in Examples below, compared to a production scale of the temperature responsive polypeptide material by a gene recombination, only one to several syntheses in a small-scale experiment facility enables production of a temperature responsive material in an amount comparable to that for production facilities for a large-scale gene recombination method. In addition, an objective substance in 100-fold or more can be obtained compared to a chemical synthesis method which has been conventionally reported (Arad & Goodman, Biopolymers, 1990, Vol. 29, page 1633).

On the other hand, the polymerization reaction of the compound represented by the general formula (I) can be performed by a general amide condensation reaction. In the case where an amino acid having a reactive side chain is included, it is preferred to protect the side chain and perform the polymerization reaction.

In addition, an extension reaction of unit by unit called a segment condensation can also be used.

The compound and the polymer compound of the present invention may have a protecting group. However, if an amino acid residue in at least one of the N terminal and C terminal is deprotected, the compound and the polymer compound are suitable for dissolution in aqueous environment.

The compound and the polymer compound of the present invention may have another compound or material linked to the terminal. The terminal may be one of the amino terminal and the carboxy terminal, and may be both of them.

As the another compound or material, a hydroxy acid sequence, an amino acid sequence, a sugar chain sequence, a protein, a polysaccharide, a metal complex, a polymer carrier, a gel, a film, a latex particle, a metal fine particle, or a plastic plate may be used. The compound and the polymer compound of the present invention can be linked to the another compound or material through a covalent bond, a coordinate bond, an ion bond, a hydrophobic interaction, a hydrogen bond, or the like.

The compound and the polymer compound of the present invention may form a composition in a solvation state, a gel state, a suspension, a uniform solution, or a phase separation state by mixing with water, a buffer solution, a salt solution, or a water-containing organic solvent.

The compound and the polymer compound of the present invention preferably have temperature responsiveness. The temperature responsiveness refers to a property that the compound aggregates by heating from the first temperature at a lower temperature side to the second temperature at a higher temperature side in, for example, water, a buffer solution, a salt solution, or a water-containing organic solvent. The first temperature and the second temperature vary depending on the kind of the amino acids contained in the polymer compound or the kind of the another compound linked to the terminal, and are appropriately set according to each polymer compound. The difference between the second temperature and the first temperature is preferably 10° C. or more.

The aggregation can be confirmed by visual observation or transmittance change obtained by using a spectrophotometer, or apparent absorbance change.

In addition, the compound and the polymer compound of the present invention preferably have reversible temperature responsiveness that water molecules are released by heating and water molecules are incorporated by cooling.

With the property, the compound and the polymer compound of the present invention can be used for production of the temperature responsive composition.

As the temperature responsive composition, the compound of the present invention (depsipeptide or a polymer thereof) or the compound of the present invention linked to the another compound or the material is used alone or used in combination with a physiologically acceptable carrier.

The physiologically acceptable carrier is not particularly limited and may be a solid formulation such as a powder and a powdered drug. The compound of the present invention is generally used as a liquid formulation by being combined with a liquid carrier. That is, examples of the liquid carrier for the liquid formulation include water, a physiological salt solution, a buffer solution (such as phosphate buffer solution), an aqueous solution of alcohol (such as an aqueous solution of ethanol), an aqueous solution of polyalcohol (such as a 5% aqueous solution of glycerin, an aqueous solution of ethylene glycol, and an aqueous solution of propylene glycol), an aqueous solution of sugar (such as a 5% aqueous solution of glucose or an aqueous solution of glucose), and an aqueous solution of albumin (such as a 5% aqueous solution of alubumin). The liquid formulation may be a solution, a suspension, an emulsion, an ointment, an air-sol formulation, a patch (a paste and a poultice). The concentration of the temperature responsive material (or a temperature responsive polymer) in the liquid formulation can be selected from, according to the solution viscosity of the polymer or the like, for example, the range of 0.1 to 90 wt %, preferably 0.5 to 50 wt %, more preferably 1 to 30 wt % (for example, 1 to 15 wt %), and particularly preferably about 1 to 10 wt %.

The temperature responsive composition may contain various physiologically or pharmacologically acceptable additives such as polymers including polyvinyl pyrrolidone, macrogol, polyvinyl alcohol, cellulose derivatives (cellulose ethers), a preservative, a stabilizer, an emulsifier, a suspending agent, a pH adjustor, a buffer agent, a drug (such as a bacteriocide, a disinfectant, an antibacterial agent, an antiviral agent, an antiinflammation agent, an anti allergy agent, an analgesic, and a hemostat), and the like.

The temperature responsive composition of the present invention has a property that the composition aggregates in response to temperature (for example, change from a state of liquid to gel). In addition, the composition has an advantage of high stability in an organism. Therefore, by applying the composition to the organism (for example, an affected area), a gel-like coated film can be formed on an applied part. The polymer and the composition of the present invention can be applied to constitution of a composition which is degraded and absorbed in an organism, a composition which is degraded and absorbed under an environment such as soil, a cell adhesion agent, a wound cover material, a microcapsule, a biomachine, a biosensor, a separation membrane, a test kit, or the like. These can be easily developed based on the related research by the inventors of the present invention (for example, Yoshida et al., Advanced Materials, 1997, Vol. 9, page 757; Hiroki et al., Journal of Polymer Science, 1998, Vol. 36, page 1495; JP 07-233194 A; Yoshida et al., Drug Design and Delivery, 1991, Vol. 7, page 159; Mashita et al., The KITAKANTO Medical Journal, 1991, Vol. 41, page 311).

EXAMPLES

Hereinafter, a method of synthesizing a -Gly-Ile-Gly-Lac-Pro-(SEQ ID NO: 7) unit which is an embodiment of the present invention and a method of synthesizing a polymer compound, i.e. poly(Gly-Ile-Gly-Lac-Pro) (SEQ ID NO: 7), which is obtained by using the unit, are described in detail in Examples 1 and 2, respectively. In addition, as other embodiments, a method of synthesizing a -Ala-Ile-Gly-Lac-Pro (SEQ ID NO: 8)- unit, a method of synthesizing poly(Ala-Ile-Gly-Lac-Pro (SEQ ID NO: 8)), and a method of synthesizing a -(Ala-Ile-Gly-Lac-Pro (SEQ ID NO: 8))$_n$- (n=2, 3, 4) oligomer are described in detail in Examples 3, 4, and 5, respectively. A method of synthesizing a -Gly-Val-Gly-Lac-Pro- (SEQ ID NO: 9) unit and a method of synthesizing a polymer compound, i.e. poly(Gly-Val-Gly-Lac-Pro) (SEQ ID NO: 9), which is obtained by using the unit, are described in detail in Example 9. In addition, the common operations in carrying out the syntheses are described as synthesis procedures 1 to 3. However, the following specific examples do not limit the present invention and the synthesis method can be, of course, changed appropriately, e.g. the protecting group or the condensation agent may be substituted with another conventional one.

Other depsipeptide unit, that is, for example, the introduction of an arbitrary amino acid residue into $X_1$ and $X_2$ in -$X_1$-$X_2$-Gly-Lac-Pro- (SEQ ID NO: 6), can be conducted in the same manner except that a corresponding N-α-t-butoxycarbonyl-amino acid is used in place of N-α-t-butoxycarbonyl-L-glycine (or N-α-t-butoxycarbonyl-L-alanine) and N-α-t-butoxycarbonyl-L-isoleucine in Examples.

The following abbreviations were used in the Examples below.

(Amino acid derivative)
Boc-Gly-OH: N-α-t-butoxycarbonyl-glycine
Boc-Ala-OH: N-α-t-butoxycarbonyl-L-alanine
Boc-Ile-OH: N-α-t-butoxycarbonyl-L-isoleucine
HCl.H-Pro-OBzl: L-proline benzyl ester hydrochloride (Hydroxycarboxylic acid)
H-Lac-OH: L-lactic acid
 (Protecting group of main chain and side chain in amino acid)
Boc: tert-butoxycarbonyl (t-Bu-O—CO—)
OBzl: benzyl (—O—CH$_2$—C$_6$H$_5$)
 (Reagent for peptide synthesis and related compounds thereof)
DCC: N,N'-dichlorohexyl carbodiimide
DCUrea: dicyclohexyl urea
HOSu: N-hydroxysuccine imide
HOBt: 1-hydroxybenzotriazole
TFA: trifluoroacetate
(Boc)$_2$O: di-t-butylcarbonate
NMM: N-methyl morpholine
EDC.HCl: 1-ethyl-3-(3-dimethylaminopropyl)-carbodiimide hydrochloride
DMAP: N,N'-dimethyl aminopyridine
 (Solvent)
THF: tetrahydrofuran
CHCl$_3$: chloroform
CDCl$_3$: deuterated chloroform
AcOEt: ethyl acetate
DMF: N,N'-dimethyl formamide
DMSO-d$_6$: deuterated dimethyl sulfoxide
MeOH: methanol
Et$_2$O: diethyl ether
 (Others)
TLC: thin layer chromatography

[Synthesis Procedure 1: Synthesis of Boc-L-Amino Acid]

An L-amino acid or an L-amino acid having a protected side chain (1.0 mol) was dissolved in 4M NaOH (250 mL, 1.0 mol). (Boc)$_2$O (240.0 g, 1.1 mol) dissolved in a minimum amount of dioxane was gradually added over 30 minutes while cooled gradually with ice MeOH. The resultant was stirred in an ice bath for 1 hour and then at room temperature for 1 hour and a half. After separating precipitated NaHCO$_3$ by filtration, the pH of the filtrate was set to 3.0 followed by extraction with AcOEt. The extracted solution was washed with a 10% aqueous solution of citric acid, and dried with Na$_2$SO$_4$. After a desiccant was separated by filtration, the filtrate was concentrated under reduced pressure. Then, hexane was added to the residue, whereby crystallization was performed. After that, the crystal was recrystallized with AcOEt-hexane, whereby Boc-L-amino acid was obtained.

[Synthesis Procedure 2: Deprotection Reaction of Amino Terminal and Synthesis of Boc-deprotected Compound]

A peptide compound having an amino group protected with N-α-t-butoxycarbonyl was put in a 300-mL eggplant flask, then TFA (or 4 M HCl in dioxane solution) was added to the flask in a draft chamber and the compound was dissolved. The flask was sealed with a calcium chloride tube immediately to prevent contamination of moisture. The completion of the reaction was confirmed with TLC. The resultant was concentrated by adding distilled Et$_2$O repeatedly until TFA smell (or hydrochloric acid smell) disappeared, whereby a TFA salt (or a hydrochloride salt) as a white powder was obtained finally. The yield was almost quantitative.

[Synthesis Procedure 3: Condensation Reaction]

The peptide compound (2.1 mmol) having the amino group protected with N-α-t-butoxycarbonyl and the deprotected carboxyl terminal was put in a 300-mL Erlenmeyer flask and dissolved in distilled CHCl$_3$. Then, HOBt (0.28 g, 2.1 mmol) and EDC.HCl (0.40 g, 2.1 mmol) (or DCC (0.43 g, 2.1 mmol)) were added thereto and the mixture was stirred. Next, the peptide compound (1.4 mmol) of the TFA salt having the amino group deprotected by the synthesis procedure 2 above was put in a 300-ml eggplant flask, and the TFA salt was neutralized with NMM. The neutralization can be confirmed with almost equivalent mole of TFA salt (0.15 mL, 1.40 mmol), but in the case of a salt having bad crystallinity, the amount of the NMM may become slightly larger. The solutions were mixed together under stirring while the solutions were cooled with ice immediately to start a reaction. The temperature of the mixture was returned to room temperature slowly and the mixture was stirred overnight. The mixture was concentrated with an evaporator and dissolved in AcOEt, and then (in the case of using DCC, DCUrea insoluble to AcOEt was removed), washed with a 10% aqueous solution of citric acid, distilled water, a saturated aqueous solution of NaHCO$_3$, distilled water, and a saturated salt solution in the stated order. Then, the resultant was dried with Na$_2$SO$_4$ and concentrated, whereby a condensation product as an oil-like substance or colorless powder was obtained. The obtained product was purified by a silica gel chromatography (distilled CH$_3$Cl-hexane or AcOEt-benzene) or a gel permeation chromatography (manufactured by Amersham Pharmacia Biotech. LH20, DMF or MeOH). In the case of the colorless powder, the powder may be purified by recrystallization using a solvent system such as AcOEt-distilled Et$_2$O or distilled CH$_3$Cl-hexane. The powder can be obtained with a yield in a range of about 70 to 90%.

Example 1

(1) Synthesis of Boc-Gly-Ile-Gly-Lac-Pro (SEQ ID NO: 7)-OBzl (1a: Synthesis of Boc-Gly-OSu)

Boc-Gly-OH (1.54 g, 8.82 mmol) was put in a 500-mL eggplant flask and dissolved in distilled CHCl$_3$. Then, DCU (2.18 g, 10.6 mmol) and HOSu (1.21 g, 10.6 mmol) were added thereto, and the stirring was started under cooling. After having been left standing overnight, the completion of the reaction was confirmed with TLC and the resultant was concentrated. After filtered, DCUrea was dissolved in AcOEt and the reprecipitated DCUrea was filtered. After that, the filtrate was concentrated and recrystallized with AcOEt-distilled Et$_2$O twice, whereby Boc-Gly-OSu was obtained. The yield was 1.74 g (63.9%). $^1$H NMR (CDCl$_3$, 300 MHz): 5.04 (1H, Boc-Gly NH); 4.27, 4.23 (2H, Gly αCH$_2$); 2.79 (4H, OSu); 1.40 (9H, Boc t-Bu).

(1b: Synthesis of HCl.H-Pro-OBzl)

Benzyl alcohol (200 mL) was put in a 1-L three-necked, round bottom flask in an exhaust hood, followed by stirring under cooling. Then, thionyl chloride (20.0 g, 0.168 mol) was dropped slowly over 1 hour. After the completion of dropping, the mixture was stirred for 10 minutes, and proline (28.8 g, 0.250 mol) was then added. The temperature of the reaction system was returned to room temperature slowly, and stirring of the resultant was continued for 48 hours. Benzyl alcohol was removed with a rotary evaporator, and the resultant was crystallized by adding distilled Et$_2$O. Purification was performed by repeating recrystallization with heat ethanol. The yield was 45.1 g (74.7%). $^1$H NMR (CDCl$_3$, 300 MHz): 7.30 (5H, -OBzl C$_6$H$_5$); 5.21 (2H, OBzl —CH$_2$—); 4.80 (1H, Pro αCH); 3.51 (2H, Pro δCH$_2$); 2.20, 1.90 (2H, Pro βCH$_2$); 1.99 (2H, Pro γCH$_2$).

(1c: Synthesis of Boc-Gly-Lac-OH)

Boc-Gly-OSu (27.2 g, 100 mmol) and DMAP (4.89 g, 40.0 mmol) were put in a 500-mL eggplant flask and dissolved in 100 ml of distilled THF. In this time, a slight of residue that had not been dissolved was dissolved by adding 1 mL of acetonitrile. H-Lac-OH (10.81 g, 120 mmol) was put in another 300-mL eggplant flask and dissolved in distilled THF, and neutralized with pyridine (9.67 mL, 120 mmol). The resultant was added in the 500-mL eggplant flask cooled with ice. One hour later, the temperature of the reacted mixture was returned to room temperature, and stirring was continued. 44 hours after the starting of the reaction, a slight of unreacted product was confirmed with TLC, but the solvent was distilled off under reduced pressure. The residue was added with EtOAc, and washed with a 10% aqueous solution of citric acid four times and distilled water twice. After the washing, an objective product was extracted three times in an aqueous phase with a saturated aqueous solution of sodium hydrogen carbonate and about 150 mL of 4 M aqueous solution of hydrochloric acid were added to the aqueous phase while the mixture was stirred under ice cooling, whereby the pH of the mixture was set to 2 to 3. After that, the objective product was extracted with EtOAc. After the completion of the extraction was confirmed with TLC, $Na_2SO_4$ was added to an organic layer and the organic layer was dried. After the desiccant was separated by filtration, the filtrate was concentrated, whereby an objective Boc-Gly-Lac-OH was obtained as a colorless oil. The yield was 13.08 g (52.9%). $^1$H NMR ($CDCl_3$, 300 MHz): 7.90 (1H, Lac —COOH); 6.31 (1H, Lac αCH); 5.19 (1H, Gly NH); 3.98, 3.77 (2H, αCH$_2$); 1.55 (3H, Lac βCH$_3$); 1.45 (9H, Boc t-Bu).

(1d: Synthesis of Boc-Gly-Lac-Pro-OBzl)

Distilled chloroform was added to a 500-mL eggplant flask containing Boc-Gly-Lac-OH (7.17 g, 28.8 mmol) and Boc-Gly-Lac-OH was dissolved. Then, DCC (6.54 g, 31.7 mmol) and HOBt (4.86 g, 31.7 mmol) were added thereto. HCl.H-Pro-OBzl (7.66 g, 31.7 mmol) was put in another 300-mL eggplant flask and dissolved with distilled chloroform. The mixture was confirmed to be neutral by adding NMM (2.84 mL, 34.1 mmol), and then added to a 500-mL eggplant flask. After stirring under ice cooling for 1 hour, the temperature of the reaction system was returned to room temperature, followed by stirring for additional 42 hours. After the completion of the reaction was confirmed with TLC, precipitated DCUrea was separated by filtration and concentrated. The residue was added with AcOEt and stored under cooling for 30 minutes. The reprecipitated DCUrea was separated by filtration, and the filtrate was added with a 10% aqueous solution of citric acid, followed by stirring for 1 hour. The resultant was transferred to a separating funnel and washed with a 10% aqueous solution of citric acid three times, water twice, a saturated aqueous solution of $NaCO_3$ twice, distilled water twice, and a saturated aqueous solution of NaCl once, followed by drying with $Na_2SO_4$. The desiccant was separated by filtration and the filtrate was concentrated under reduced pressure. Benzene was added to the residue and dehydration operations were performed three times. The residue was not crystallized even by adding hexane, and purified by a silica gel column chromatography (developing solvent; AcOEt-benzene=1:3 (=v/v)), whereby Boc-Gly-Lac-Pro-OBzl as an objective product was obtained as a pale yellow oil. The yield was 5.95 g (yield 47.6%). $^1$H NMR ($CDCl_3$, 300 MHz): 7.37 (5H, -OBzl $C_6H_5$); 5.21 (1H, Lac αCH); 5.19, 5.16 (2H, OBzl —CH$_2$—); 5.20, 5.18 (1H, Gly NH); 5.07 (1H, Pro αCH); 4.61, 4.59 (2H, Gly αCH$_2$); 3.95, 3.93 (2H, Pro δCH$_2$); 3.73, 3.68 (2H, Pro βCH$_2$); 3.55, 3.54 (2H, Pro γCH$_2$); 1.46 (9H, Boc t-Bu); 1.24 (3H, Lac βCH$_3$).

(1e: Synthesis of Boc-Ile-Gly-Lac-Pro-OBzl)

HCl.H-Gly-Lac-Pro-OBzl (5.42 g, 14.6 mmol), NMM (1.61 ml, 14.6 mmol), Boc-Ile-OH.1/2$H_2O$ (4.21 g, 17.52 mmol), EDC.HCl (3.36 g, 17.52 mmol), and HOBt (2.68 g, 17.52 mmol) were used to cause a condensation reaction, whereby a yellow oil was obtained. The yield was 8.61 g (yield ~100%). $^1$H NMR (DMSO-$d_6$, 300 MHz): 8.30 (1H, Gly NH); 7.35 (5H, -OBzl $C_6H_5$); 6.65 (1H, Ile NH); 5.21 (1H, Lac αCH); 5.19, 5.16 (2H, OBzl —CH$_2$—); 4.39 (1H, Pro αCH); 3.99 (1H, Ile αCH); 3.85, 3.82 (2H, Gly αCH$_2$); 3.78, 3.76 (2H, Pro δCH$_2$); 2.19, 2.13 (2H, Pro βCH$_2$); 1.94, 1.92 (2H, Pro γCH$_2$); 1.36 (9H, Boc t-Bu); 1.27 (3H, Lac βCH$_3$); 1.08 (2H, Ile γCH$_2$); 0.83 (3H, Ile γCH$_3$); 0.77 (3H, Ile δCH$_3$).

Example 2

(2) Synthesis of poly(Gly-Ile-Gly-Lac-Pro) (SEQ ID NO: 7)

(2a: Synthesis of Boc-Gly-Ile-Gly-Lac-Pro (SEQ ID NO: 7)-OBzl)

HCl.H-Ile-Gly-Lac-Pro-OBzl (3.28 g, 6.80 mmol), NMM (0.75 mL, 6.80 mmol), Boc-Gly-OH (1.31 g, 7.50 mmol), EDC.HCl (1.44 g, 7.50 mmol), and HOBt (1.15 g, 7.50 mmol) were used to cause a condensation reaction, whereby a yellow oil was obtained. The yield was 3.45 g (yield 83.9%). $^1$H NMR (DMSO-$d_6$, 500 MHz): 8.51 (1H, Gly$^1$ NH); 7.66 (1H, Ile NH); 7.35 (5H, -OBzl $C_6H_5$); 7.00 (1H Gly$^3$ NH); 5.21 (1H, Lac αCH); 5.11, 5.08 (2H, OBzl —CH$_2$—); 4.35 (1H, Pro αCH); 4.20 (1H, Ile αCH); 3.94, 3.93 (2H, Gly$^3$ αCH$_2$); 3.77, 3.76 (2H, Gly$^1$ αCH$_2$); 3.51, 3.49 (2H, Pro δCH$_2$); 2.19, 2.17 (2H, Pro βCH$_2$); 1.93, 1.91 (2H, Pro γCH$_2$); 1.34 (9H, Boc t-Bu); 1.26 (3H, Lac βCH$_3$); 1.03 (2H, Ile γCH$_2$); 0.83 (3H, Ile γCH$_3$); 0.77 (3H, Ile δCH$_3$).

(2b: Synthesis of Boc-Gly-Ile-Gly-Lac-Pro (SEQ ID NO: 7)—OH)

Boc-Gly-Ile-Gly-Lac-Pro (SEQ ID NO: 7)-OBzl (3.45 g, 5.71 mmol) was put in a 300-mL eggplant flask and methanol was added to make a solution. After two microspatulas of palladium carbon powder were added thereto, the whole system was substituted with hydrogen gas, followed by a catalytic reduction reaction for 11 hours. After the completion of the reaction, 5% palladium carbon was separated by filtration, and the solvent was distilled off under reduced pressure. Benzene was added to the residue and dehydration operation by azeotropy was conducted three times. Hexane was added to the residue, whereby the residue was crystallized. The crystal was collected by filtration and dried under reduced pressure, whereby an objective product was obtained. The yield was 2.55 g (yield 87.0%). $^1$H NMR (DMSO-$d_6$, 300 MHz): 8.50 (1H, Gly$^1$ NH); 7.64 (1H, Ile NH); 6.97 (1H, Gly$^3$ NH); 5.21 (1H, Lac αCH); 4.73 (1H, Pro αCH); 4.21 (1H, Ile αCH); 3.99, 3.97 (2H, Gly$^3$ αCH$_2$); 3.81, 3.79 (2H, Gly$^1$ αCH$_2$); 3.51, 3.49 (2H, Pro δCH$_2$); 2.19, 2.17 (2H, Pro βCH$_2$); 2.03, 2.01 (2H, Pro γCH$_2$); 1.32 (9H, Boc t-Bu); 1.24 (3H, Lac βCH$_3$); 1.04 (2H, Ile γCH$_2$); 0.83 (3H, Ile γCH$_3$); 0.77 (3H, Ile δCH$_3$).

(2c: Synthesis of Boc-Gly-Ile-Gly-Lac-Pro (SEQ ID NO: 7)-OSu)

Boc-Gly-Ile-Gly-Lac-Pro (SEQ ID NO: 7)—OH (2.55 g, 4.95 mmol) and HOSu (0.57 g, 4.95 mmol) were added to a 300-mL eggplant flask, and dissolved in distilled THF. While the mixture was stirred under ice cooling, DCC (1.12 g, 5.45 mmol) was added to the mixture, followed by stirring under ice cooling for 1 hour and then at room temperature for 24 hours. After the completion of the reaction was confirmed with TLC, DCUrea was separated by filtration, and the filtrate was concentrated under reduced pressure. The residue was added with ethyl acetate and left at stand in a refrigerator for 1 day. The produced DCUrea was separated by filtration and the filtrate was concentrated under reduced pressure again. After distilled THF was added to the residue, the residue was crystallized with hexane. Then, the residue was recrystallized from distilled THF-hexane. The yield was 3.12 g (yield −100%). $^1$H NMR (DMSO-d$_6$, 300 MHz): 8.50 (1H, Gly$^1$ NH); 7.42 (1H, Ile NH); 6.97 (1H, Gly$^3$ NH); 5.21 (1H, Lac αCH); 4.73 (1H, Pro αCH); 4.21 (1H, Ile αCH); 3.99, 3.97 (2H, Gly$^3$ αCH$_2$); 3.81, 3.79 (2H, Gly$^1$ αCH$_2$); 3.51, 3.49 (2H, Pro δCH$_2$); 2.19, 2.17 (2H, Pro βCH$_2$); 2.03, 2.01 (2H, Pro γCH$_2$); 2.78 (4H, OSu); 1.32 (9H, Boc t-Bu); 1.24 (3H, Lac βCH$_3$); 1.04 (2H, Ile γCH$_2$); 0.84 (3H, Ile γCH$_3$); 0.78 (3H, Ile δCH$_3$).

(2d: Synthesis of HCl.H-Gly-Ile-Gly-Lac-Pro (SEQ ID NO: 7)-OSu)

The amino terminal of Boc-Gly-Ile-Gly-Lac-Pro (SEQ ID NO: 7)-OSu (3.03 g, 4.95 mmol) was deprotected with 4M HCl/dioxane (15 mL), whereby a colorless powder was obtained. The yield was 2.57 g (yield 94.5%).

(2e: Synthesis of poly(Gly-Ile-Gly-Lac-Pro) (SEQ ID NO: 7))

HCl.H-Gly-Ile-Gly-Lac-Pro (SEQ ID NO: 7)-OSu (2.57 g, 4.69 mmol) was put in a 100-mL eggplant flask and dissolved in 40 mL of distilled DMF. Triethylamine (0.65 mL, 4.69 mmol) was added to start a reaction. The mixture was stirred at room temperature for 2 weeks. After the completion of the reaction, DMF was distilled off under reduced pressure with a vacuum pump. When distilled water was dropped thereto, a colorless solid was produced and separated by filtration. After salt was added to the filtrate, extraction was performed with chloroform four times. After an organic layer was concentrated under reduced pressure, dry ether was added thereto to crystallize the resultant. The crystal was collected by filtration. The yield was 0.98 g (yield 46.2%).

From a mass spectrometry by MALDI-TOF method described below, the polymerization degree of the obtained polymer was about 3 (the molecular weight was about 1,200).

Example 3

(3) Synthesis of Boc-Ala-Ile-Gly-Lac-Pro (SEQ ID NO: 8)-OBzl (3a: Synthesis of Boc-Ala-Ile-Gly-Lac-Pro (SEQ ID NO: 8)-OBzl)

HCl.H-Ile-Gly-Lac-Pro-OBzl (3.96 g, 8.18 mmol), NMM (0.90 mL, 8.18 mmol), Boc-Ala-OH (1.86 g, 9.82 mmol), EDC.HCl (1.88 g, 9.82 mmol), and HOBt (1.50 g, 9.82 mmol) were used to cause a condensation reaction, whereby a colorless crystal was obtained. The yield was 4.93 g (yield 58.1%). $^1$H NMR (DMSO-d$_6$, 300 MHz): 8.47 (1H, Gly NH); 7.53 (1H, Ile NH); 7.34 (5H, -OBzl C$_6$H$_5$); 7.02 (1H, Ala NH); 5.21 (1H, Lac αCH); 5.17, 5.14 (2H, OBzl —CH$_2$—); 4.38 (1H, Pro αCH); 4.20 (1H, Ile αCH); 3.98, 3.94 (2H, Gly αCH$_2$); 3.86 (1H, Ala αCH); 3.64, 3.61 (2H, Pro δCH$_2$); 2.19, 2.17 (2H, Pro βCH$_2$); 1.93, 1.91 (2H, Pro γCH$_2$); 1.36 (9H, Boc t-Bu); 1.31 (3H, Ala βCH$_3$); 1.13 (3H, Lac βCH$_3$); 1.03 (2H, Ile γCH$_2$); 0.83 (3H, Ile γCH$_3$); 0.77 (3H, Ile δCH$_3$).

Example 4

(4) Synthesis of poly(Ala-Ile-Gly-Lac-Pro) (SEQ ID NO: 8)

(4a: Synthesis of Boc-Ala-Ile-Gly-Lac-Pro (SEQ ID NO: 8)—OH)

Boc-Ala-Ile-Gly-Lac-Pro (SEQ ID NO: 8)-OBzl (3.34 g, 5.39 mmol) was put in a 300-mL eggplant flask and dissolved by adding methanol. After two microspatulas of 5% palladium carbon powder were added thereto, the whole system was substituted with hydrogen gas, followed by a catalytic reduction reaction for 11 hours. After the completion of the reaction, 5% palladium carbon was separated by filtration, and the solvent was distilled off under reduced pressure. Benzene was added to the residue and dehydration operation by azeotropy was conducted three times. A slight amount of ethyl acetate was added to the residue, and hexane was then added to the residue, whereby the residue was crystallized. The crystal was collected by filtration and dried under reduced pressure, whereby an objective product was obtained.

The yield was 2.20 g (yield 77.2%). $^1$H NMR (DMSO-d$_6$, 300 MHz): 8.46 (1H, Gly NH); 7.55 (1H, Ile NH); 7.01 (1H, Ala NH); 5.21 (1H, Lac αCH); 4.21 (1H, Pro αCH); 3.98 (1H, Ile αCH); 3.97, 3.96 (2H, Gly αCH$_2$); 3.72 (1H, Ala αCH); 3.59, 3.50 (2H, Pro δCH$_2$); 2.14, 2.16 (2H, Pro βCH$_2$); 1.93, 1.91 (2H, Pro γCH$_2$); 1.36 (9H, Boc t-Bu); 1.32 (3H, Ala βCH$_3$); 1.14 (3H, Lac βCH$_3$); 1.12 (2H, Ile γCH$_2$); 0.83 (3H, Ile γCH$_3$); 0.80 (3H, Ile δCH$_3$).

(4b: Synthesis of Boc-Ala-Ile-Gly-Lac-Pro (SEQ ID NO: 8)-OSu)

Boc-Ala-Ile-Gly-Lac-Pro (SEQ ID NO: 8)—OH (2.18 g, 4.12 mmol) and HOSu (0.47 g, 4.12 mmol) were put in a 300-mL eggplant flask and dissolved in distilled THF. While the mixture was stirred under ice cooling, DCC (0.93 g, 4.53 mmol) was added thereto to start a reaction. The mixture was stirred under ice cooling for 1 hour and then at room temperature for 21 hours. After the completion of the reaction was confirmed with TLC, DCUrea was separated by filtration, and the filtrate was concentrated under reduced pressure. The residue was added with AcOEt and left at stand in a refrigerator for 1 day. After the generated DCUrea was separated by filtration again, the filtrate was crystallized with hexane. Further, the resultant was recrystallized from ethyl acetate-hexane. The yield was 2.49 g (yield 96.5%). $^1$H NMR (DMSO-d$_6$, 300 MHz): 8.48 (1H, Gly NH); 7.55 (1H, Ile NH); 7.00 (1H, Ala NH); 5.24 (1H, Lac αCH); 4.73 (1H, Pro αCH); 3.97 (1H, Ile αCH); 3.78, 3.74 (2H, Gly αCH$_2$); 3.66 (1H, Ala αCH); 3.57, 3.43 (2H, Pro δCH$_2$); 2.79 (4H, OSu); 2.14, 2.16 (2H, Pro βCH$_2$); 1.93, 1.91 (2H, Pro γCH$_2$); 1.36 (9H, Boc t-Bu); 1.33 (3H, Ala βCH$_3$); 1.15 (3H, Lac βCH$_3$); 1.12 (2H, Ile γCH$_2$); 0.83 (3H, Ile γCH$_3$); 0.80 (3H, Ile δCH$_3$).

(4c: Synthesis of HCl.H-Ala-Ile-Gly-Lac-Pro (SEQ ID NO: 8)-OSu)

The amino terminal of Boc-Ala-Ile-Gly-Lac-Pro (SEQ ID NO: 8)-OSu (3.03 g, 4.95 mmol) was deprotected with 4M HCl/dioxane (15 mL), whereby a colorless powder was obtained. The yield was 2.51 g (yield ~100%).

(4d: Synthesis of poly(Ala-Ile-Gly-Lac-Pro) (SEQ ID NO: 8))

HCl.H-Ala-Ile-Gly-Lac-Pro (SEQ ID NO: 8)-OSu (1.20 g, 2.13 mmol) was added to a 100-mL eggplant flask and dissolved in 4.0 mL of distilled DMF. Triethylamine (0.30 mL, 2.13 mmol) was added thereto to start a reaction. The mixture was stirred while heated in a water bath at about 35° C. With the increase in the viscosity of the reaction system, DMF was added and the final volume was 16.0 mL. After 36 hours, when distilled water was dropped to the reaction system, a colorless solid was generated. Then, the solid was separated by filtration. After salt was added to the filtrate, the filtrate was extracted with chloroform four times. An organic layer was concentrated under reduced pressure, and then crystallized by adding dry ether. The crystal was collected by filtration. The yield was 0.20 g (yield 21.3%). The melting point was 212 to 214° C. $[α]_D^{20}$=−82.4°. From the mass spectrometry by MALDI-TOF method described below, the polymerization degree of the obtained polymer was about 10 (the molecular weight was about 4,500).

Example 5

(5) Synthesis of Boc-(Ala-Ile-Gly-Lac-Pro (SEQ ID NO: 8))$_n$-OBzl (n=2,3,4)

(5a: Synthesis of Boc-(Ala-Ile-Gly-Lac-Pro) (SEQ ID NO: 8)$_2$-OBzl)

HCl.H-Ala-Ile-Gly-Lac-Pro (SEQ ID NO: 8)-OBzl (2.55 g, 4.58 mmol), NMM (0.51 mL, 4.58 mmol), Boc-Ala-Ile-Gly-Lac-Pro (SEQ ID NO: 8)—OH (2.67 g, 5.05 mmol), EDC.HCl (0.97 g, 5.05 mmol), and HOBt (0.77 g, 5.05 mmol) were used to cause a condensation reaction, whereby a colorless crystal was obtained. The yield was 3.70 g (yield 77.20). The melting point was 159 to 161° C. $[\alpha]_D^{20} = -160.6°$. $^1$H NMR (DMSO-d$_6$, 500 MHz): 8.50 (1H, Gly$^3$ NH); 8.45 (1H, Gly$^8$ NH); 8.04 (1H, Ala$^6$ NH); 7.61 (1H, Ile$^7$ NH); 7.57 (1H, Ile$^2$ NH); 7.34 (5H, -OBzl C$_6$H$_5$); 7.05, 6.55 (1H Ala$^1$ NH); 5.21 (2H, Lac$^4$, Lac$^9$ αCH); 5.10, 5.05 (2H, OBzl —CH$_2$—); 4.40, 4.30 (2H, Pro$^5$, Pro$^{10}$ αCH); 4.25 (1H, Ala$^6$ αCH); 4.20 (2H, Ile$^2$, Ile$^7$ αCH); 4.00 (1H, Ala$^1$ αCH); 3.98, 3.97 (2H, Gly$^3$, Gly$^8$ αCH$_2$); 3.70, 3.72 (2H, Gly$^3$, Gly$^8$ αCH$_2$); 3.57, 3.53 (4H, Pro$^5$, Pro$^{10}$ δCH$_2$); 2.14, 2.04 (4H, Pro$^5$, Pro$^{10}$ βCH$_2$); 1.91, 1.80 (4H, Pro γCH$_2$); 1.65 (2H, Ile$^2$, Ile$^7$ γCH$_2$); 1.36 (9H, Boc t-Bu); 1.30 (3H, Lac$^9$ βCH$_3$); 1.25 (3H, Lac$^4$ βCH$_3$); 1.15 (6H, Ala$^1$, Ala$^6$ βCH$_3$); 1.12 (2H, Ile$^2$, Ile$^7$ γCH$_2$); 0.83 (6H, Ile$^2$, Ile$^7$ γCH$_3$); 0.80 (6H, Ile$^2$, Ile$^7$ γCH$_3$).

(5b: Synthesis of HCl.H-(Ala-Ile-Gly-Lac-Pro (SEQ ID NO: 8))$_2$-OBzl)

The amino terminal of Boc-(Gly-Ile-Gly-Lac-Pro (SEQ ID NO: 7))$_2$-OBzl (1.20 g, 1.15 mmol) was deprotected with 4M HCl/dioxane (2.9 mL), whereby a colorless powder was obtained. The yield was 1.02 g (yield 91.1%).

(5c: Synthesis of Boc-(Ala-Ile-Gly-Lac-Pro (SEQ ID NO: 8))$_3$-OBzl)

HCl.H-(Ala-Ile-Gly-Lac-Pro (SEQ ID NO: 8))$_2$-OBzl (1.02 g, 0.97 mmol), NMM (0.118 mL, 0.970 mmol), Boc-Ala-Ile-Gly-Lac-Pro (SEQ ID NO: 8)—OH (0.570 g, 1.07 mmol), EDC.HCl (0.220 g, 1.07 mmol), and HOBt (0.145 g, 1.07 mmol) were used to cause a condensation reaction, whereby a colorless crystal was obtained. The yield was 0.90 g (yield 62.8%). The melting point was 190 to 192° C. $[\alpha]_D^{20} = -148.8°$. $^1$H NMR (DMSO-d$_6$, 500 MHz): 8.48 (1H, Gly$^3$ NH); 8.43 (1H, Gly$^8$, Gly$^{13}$ NH); 8.05 (1H, Ala$^6$, Ala$^{11}$ NH); 7.65 (2H, Ile$^7$, Ile$^{12}$ NH); 7.55 (1H, Ile$^2$ NH); 7.34 (5H, -OBzl C$_6$H$_5$); 7.05, 6.53 (1H, Ala$^1$ NH); 5.20 (3H, Lac$^4$, Lac$^9$, Lac$^{13}$ αCH); 5.10, 5.05 (2H, OBzl —CH$_2$—); 4.40, 4.30 (3H, Pro$^5$, Pro$^{10}$, Pro$^{15}$ αCH); 4.25 (2H, Ala$^6$, Ala$^{11}$ αCH); 4.20 (3H, Ile$^2$, Ile$^7$, Ile$^{12}$ αCH); 3.90 (1H, Ala$^1$ αCH); 3.98, 3.97 (3H, Gly$^3$, Gly$^8$, Gly$^{13}$ αCH$_2$); 3.70, 3.72 (3H, Gly$^3$, Gly$^8$, Gly$^{13}$ αCH$_2$); 3.57, 3.53 (6H, Pro$^5$, Pro$^{10}$, Pro$^{15}$ δCH$_2$); 2.14, 2.04 (6H, Pro$^5$, Pro$^{10}$, Pro$^{15}$ βCH$_2$); 1.91, 1.80 (6H, Pro$^5$, Pro$^{10}$, Pro$^{15}$ γCH$_2$); 1.65 (3H, Ile$^2$, Ile$^7$, Ile$^{12}$ γCH$_2$); 1.36 (9H, Boc t-Bu); 1.30 (6H, Lac$^9$, Lac$^{13}$ βCH$_3$); 1.25 (3H, Lac$^4$ βCH$_3$); 1.15 (6H, Ala$^6$, Ala$^{11}$ βCH$_3$); 1.10 (3H, Ala$^1$ βCH$_3$); 1.05 (3H, Ile$^2$, Ile$^7$, Ile$^{12}$ γCH$_2$); 0.83 (9H, Ile$^2$, Ile$^7$, Ile$^{12}$ γCH$_3$); 0.75 (9H, Ile$^2$, Ile$^7$, Ile$^{12}$ γCH$_3$).

(5d: Synthesis of HCl.H-(Ala-Ile-Gly-Lac-Pro) (SEQ ID NO: 8)$_3$-OBzl)

The amino terminal of Boc-(Gly-Ile-Gly-Lac-Pro (SEQ ID NO: 7))$_3$-OBzl (1.20 g, 1.15 mmol) was deprotected with 4M HCl/dioxane (0.850 mL), whereby a colorless powder was obtained. The yield was 0.48 g (yield ~100%).

(5e: Synthesis of Boc-(Ala-Ile-Gly-Lac-Pro) (SEQ ID NO: 8)$_4$-OBzl)

HCl.H-(Ala-Ile-Gly-Lac-Pro) (SEQ ID NO: 8)$_3$-OBzl (0.48 g, 0.34 mmol), NMM (0.037 mL, 0.34 mmol), Boc-Ala-Ile-Gly-Lac-Pro (SEQ ID NO: 8)—OH (0.20 g, 5.05 mmol), EDC.HCl (0.76 g, 0.37 mmol), and HOBt (0.050 g, 0.37 mmol) were used to cause a condensation reaction, whereby a colorless powder was obtained. The yield was 0.370 g (yield 57.5%). $^1$H NMR (DMSO-d$_6$, 500 MHz): 8.48 (1H, Gly$^3$ NH); 8.43 (1H, Gly$^8$, Gly$^{13}$, Gly$^{18}$ NH); 8.05 (1H, Ala$^6$, Ala$^{11}$, Ala$^{16}$ NH); 7.65 (3H, Ile$^7$, Ile$^{12}$, Ile$^{17}$ NH); 7.55 (1H, Ile$^2$ NH); 7.34 (5H, -OBzl C$_6$H$_5$); 7.05, 6.53 (1H, Ala$^1$ NH); 5.20 (4H, Lac$^4$, Lac$^9$, Lac$^{14}$, Lac$^{18}$ αCH); 5.10, 5.05 (2H, OBzl —CH$_2$—); 4.40, 4.30 (4H, Pro$^5$, Pro$^{10}$, Pro$^{15}$, Pro$^{20}$ αCH); 4.25 (3H, Ala$^6$, Ala$^{11}$, Ala$^{16}$ αCH); 4.20 (4H, Ile$^2$, Ile$^7$, Ile$^{12}$, Ile$^{17}$ αCH); 3.90 (1H, Ala$^1$ αCH); 3.98, 3.97 (4H, Gly$^3$, Gly$^8$, Gly$^{13}$, Gly$^{18}$ αCH$_2$); 3.70, 3.72 (4H, Gly$^3$, Gly$^8$, Gly$^{13}$, Gly$^{18}$ αCH$_2$); 3.57, 3.53 (8H, Pro$^5$, Pro$^{10}$, Pro$^{15}$, Pro$^{20}$ δCH$_2$); 2.14, 2.04 (8H, Pro$^5$, Pro$^{10}$, Pro$^{15}$, Pro$^{20}$ βCH$_2$); 1.91, 1.80 (8H, Pro$^5$, Pro$^{10}$, Pro$^{15}$, Pro$^{20}$ γCH$_2$); 1.65 (4H, Ile$^2$, Ile$^7$, Ile$^{12}$, Ile$^{17}$ γCH$_2$); 1.36 (9H, Boc t-Bu); 1.30 (9H, Lac$^9$, Lac$^{14}$, Lac$^{19}$ βCH$_3$); 1.25 (3H, Lac$^4$ βCH$_3$); 1.15 (9H, Ala$^6$, Ala$^{11}$, Ala$^{16}$ βCH$_3$); 1.10 (3H, Ala$^1$ βCH$_3$); 1.05 (4H, Ile$^2$, Ile$^7$, Ile$^{12}$, Ile$^{17}$ γCH$_2$); 0.83 (12H, Ile$^2$, Ile$^7$, Ile$^{12}$, Ile$^{17}$ γCH$_3$); 0.75 (12H, Ile$^2$, Ile$^7$, Ile$^{12}$, Ile$^{17}$ γCH$_3$).

Example 6

(6) Mass Spectrometry by MALDI-TOF Method

Figure 1:
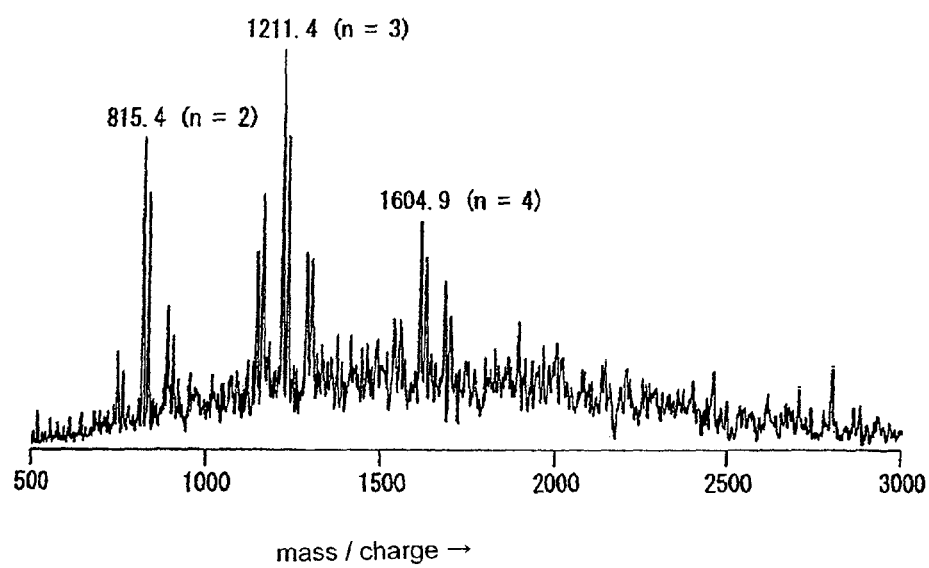
FIG. 1 illustrates a spectrum obtained by measuring poly(Gly-Ile-Gly-Lac-Pro) (SEQ ID NO: 7) which is one embodiment of the present invention by MALDI-TOF mass spectrometry.
Figure 2:
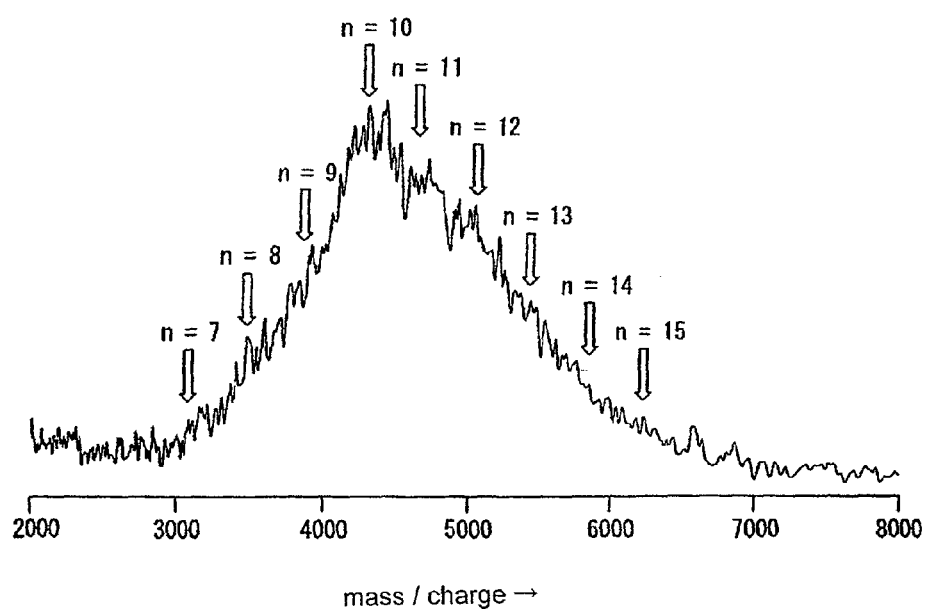
FIG. 2 illustrates a spectrum obtained by measuring poly(Ala-Ile-Gly-Lac-Pro) (SEQ ID NO: 8) which is one embodiment of the present invention by MALDI-TOF mass spectrometry.

MALDI-spectra of the polymer compounds obtained in Examples 2 and 4 were measured. With the measurement, the molecular weights of the polymer compounds synthesized by the polymerization reaction can be confirmed. Here, examples of poly(Gly-Ile-Gly-Lac-Pro (SEQ ID NO: 7)) and poly(Ala-Ile-Gly-Lac-Pro) (SEQ ID NO: 8) are shown in FIGS. 1 and 2. As a result, 2 mer to 4 mer of poly(Gly-Ile-Gly-Lac-Pro (SEQ ID NO: 7)) (mass of monomer unit=396.19) were observed. In addition, 7 mer to 15 mer of poly(Ala-Ile-Gly-Lac-Pro) (SEQ ID NO: 8) (mass of monomer unit=428.2) were observed. Presumably, from the two viewpoint that the sample used herein was not be purified with a dialysis membrane and the peak at high molecular weight changed by irradiation laser intensity, compounds having low polymerization degree were observed particularly in poly(Gly-Ile-Gly-Lac-Pro (SEQ ID NO: 7)).

Example 7

(7) Circular Dichroism Spectrum

Figure 3:
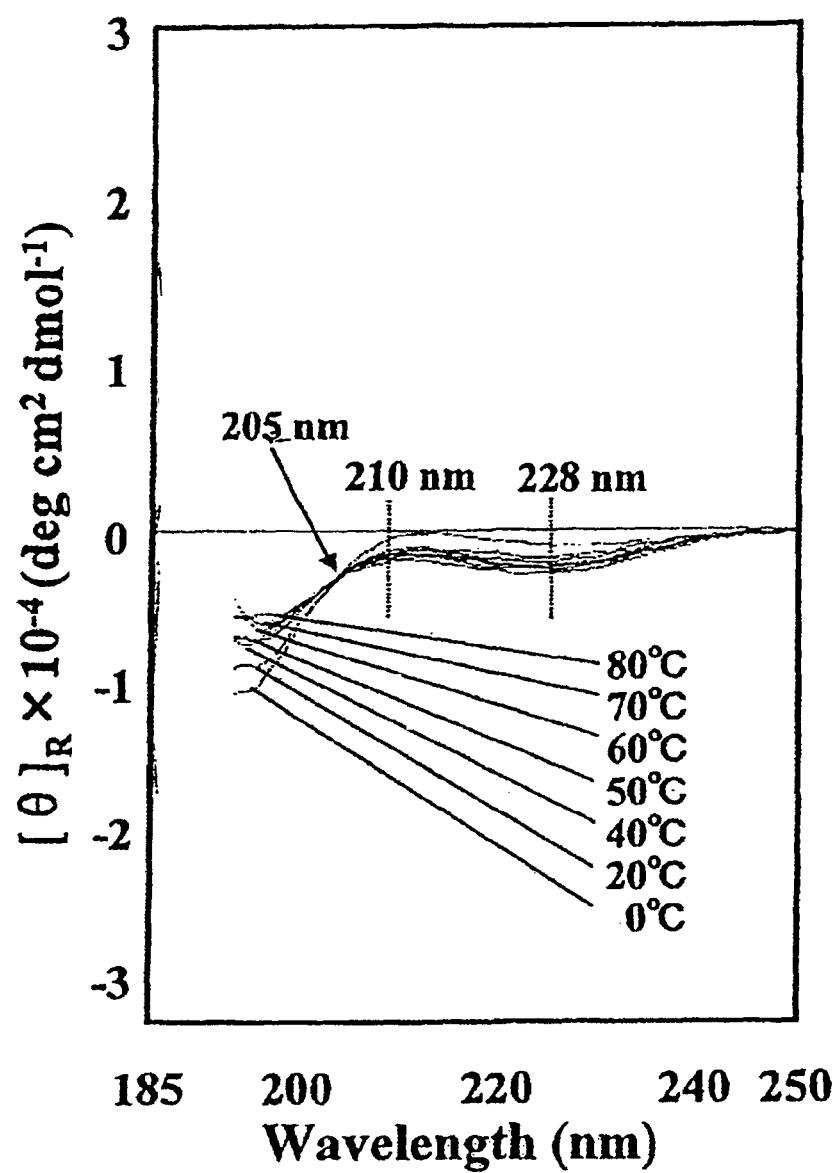
FIG. 3 illustrates circular dichroism spectra depending on temperature change. Measurement was performed according to the following procedure: an aqueous solution of poly(Gly-Ile-Gly-Lac-Pro) (SEQ ID NO: 7) (0.1 mg/mL) which is one embodiment of the present invention was put in a 1-mm-thick quartz cell for absorption spectra; the temperature was increased by every 10° C. between 0° C. and 80° C.; and a spectrum was measured when the temperature equilibrated at each temperature.
Figure 4:
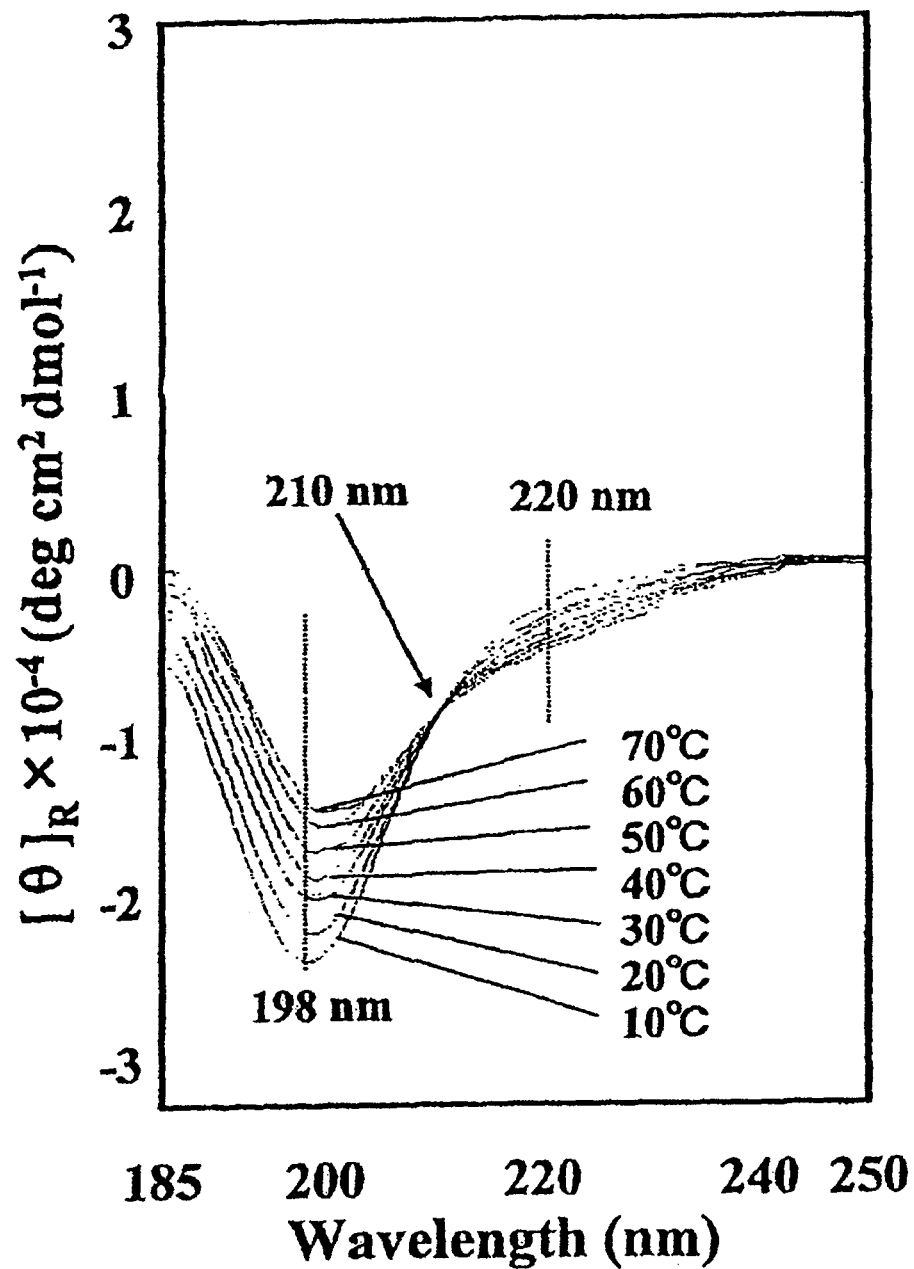
FIG. 4 illustrates circular dichroism spectra depending on temperature change. Measurement was performed according to the following procedure: an aqueous solution of poly(Ala-Ile-Gly-Lac-Pro) (SEQ ID NO: 8) (0.1 mg/mL) which is one embodiment of the present invention was put in a 1-mm-thick quartz cell for absorption spectra; the temperature was increased by every 10° C. between 10° C. and 70° C.; and a spectrum was measured when the temperature equilibrated at each temperature.

Circular dichroism spectra depending on temperature of the polymer compounds obtained in Examples 2 and 4 were measured. With the measurement, information different from the change of temperature responsiveness by visual observation can be obtained. For example, findings on solution structure can be obtained. Here, spectrum of poly(Gly-Ile-Gly-Lac-Pro (SEQ ID NO: 7)) and poly(Ala-Ile-Gly-Lac-Pro) (SEQ ID NO: 8) were shown in FIG. 3 and FIG. 4. As a result, each spectrum changes and indicates circular dichroism point at 205 nm and 210 nm. There is no aggregation because the sample is a dilute aqueous solution (0.1 mg/mL). With the increase in the temperature, the negative bands recognized at 195 nm and 198 nm were confirmed to decrease. From the related study by the inventors of the present invention, this may be because the solution structure becomes random (For example, Oku et al., Journal of Polymer Science, Part A, Polymer Chemistry, 2000, Vol. 38, page 4524 and Oku et al., Journal of Polymer Science, Part A, Polymer Chemistry, 2000, Vol. 39, page 56).

Example 8

(8) Observation of Temperature Responsiveness by Apparent Absorbance

Figure 5:
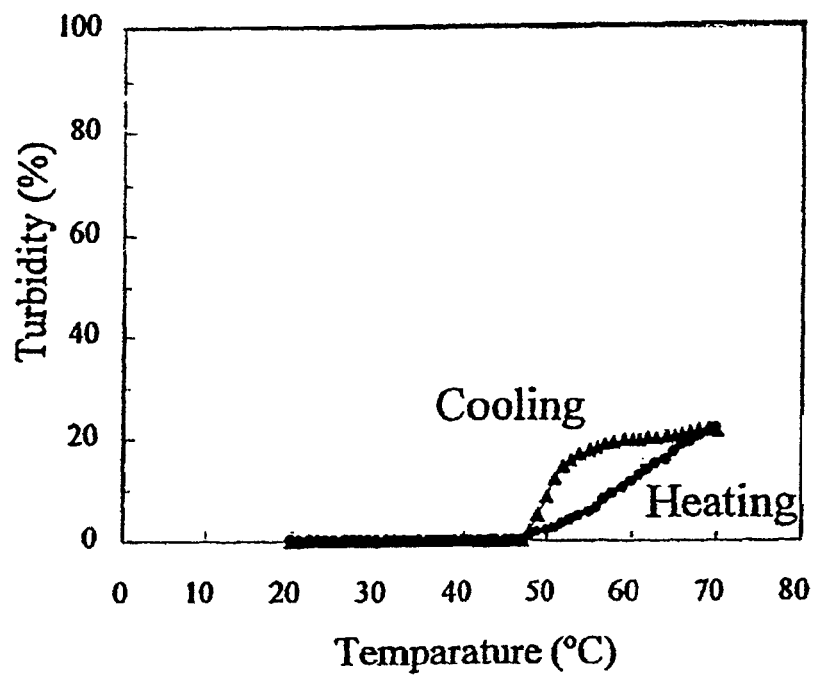
FIG. 5 illustrates a graph obtained by the following procedure: an aqueous solution of poly(Gly-Ile-Gly-Lac-Pro) (SEQ ID NO: 7) (10 mg/mL) which is one embodiment of the present invention was put in a 1-mm-thick quartz cell for absorption spectra; the temperature was increased at a rate of 1° C./5 minutes between 20° C. and 70° C. and then decreased; transmittance (%) was measured with respect to a light of 350 nm at each temperature in a 1° C. interval; and a turbidity (%) obtained by subtracting the transmittance (%) from 100 was plotted.
Figure 6:
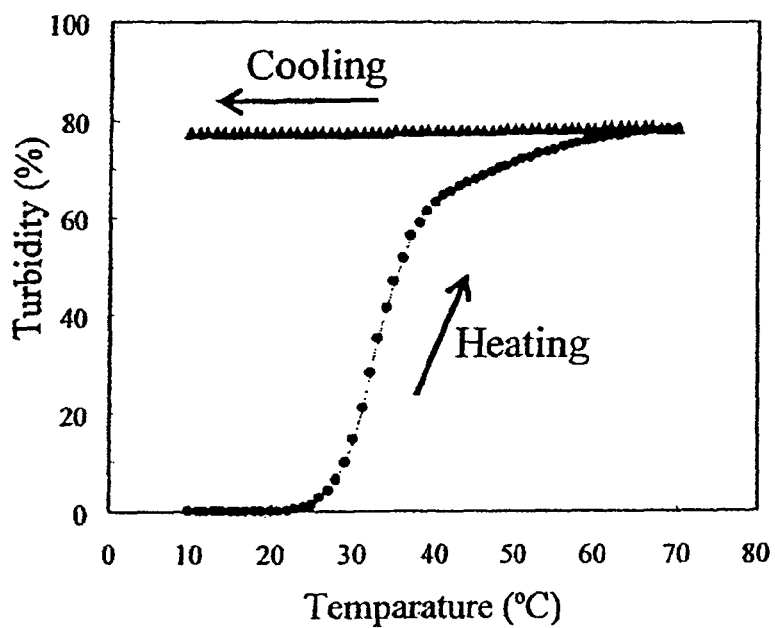
FIG. 6 illustrates a graph obtained by the following procedure: an aqueous solution of poly(Ala-Ile-Gly-Lac-Pro) (SEQ ID NO: 8) (10 mg/mL) which is one embodiment of the present invention was put in a 1-mm-thick quartz cell for absorption spectra; the temperature was increased at a rate of 1° C./5 minutes between 20° C. and 70° C. and then decreased; transmittance (%) was measured with respect to a light of 350 nm at each temperature in a 1° C. interval; and a turbidity (%) obtained by subtracting the transmittance (%) from 100 was plotted.

The change in temperature responsiveness of each polymer obtained in Examples 2 and 4 due to heating an aqueous solution of the polymer was observed by apparent absorbance. The wavelength for observation was 350 nm. The wavelength corresponds to phenomenon of light scattering, i.e. white turbidity, by visual observation. Here, spectrum of poly(Gly-Ile-Gly-Lac-Pro (SEQ ID NO: 7)) and poly(Ala-Ile-Gly-Lac-Pro) (SEQ ID NO: 8) are shown in FIG. 5 and FIG. 6, respectively. The ordinate axes each represent turbidity converted from the transmittance. From the figure, the temperature responsiveness rate can be compared. That is, in the case where the temperature-increase rate and temperature-decrease rate are 1° C./5 minutes, it was confirmed that poly(Gly-Ile-Gly-Lac-Pro (SEQ ID NO: 7)) exhibits such a reversible temperature responsiveness that the polymer causes gelation by increase in the temperature and is liquefied by cooling, and in contrast, poly(Ala-Ile-Gly-Lac-Pro) (SEQ ID NO: 8) exhibits irreversible temperature responsiveness for several hours even when cooled. In addition, in comparison between the observation by visual observation and the measured turbidity, the polymer underwent aggregation adequately even when the turbidity exceeds about 10 to 20%. In particular, poly(Ala-Ile-Gly-Lac-Pro) (SEQ ID NO: 8) is a first example of exhibiting reversibility, while not exhibiting rapid temperature responsiveness (return to a uniform solution), which is generally observed in several seconds, when an aggregation state at a high temperature is transferred to a low temperature (4° C.). The solution was actually returned to a uniform solution finally by left standing at 4° C. for 1 to 2 days. The extremely slow responsiveness (return to a uniform solution) at a low temperature is a novel property that has not happened before.

In addition, the oligodepsipeptide Boc-(Ala-Ile-Gly-Lac-Pro) (SEQ ID NO: 8)$_n$-OBzl (n=2 to 4) obtained in Example 5 became an aqueous solution easily by eliminating the protecting group at the carboxyl terminal or the amino terminal, whereby the same temperature responsiveness as the polydepsipeptide was confirmed.

Example 9

(9) Synthesis of Poly(Gly-Val-Gly-Lac-Pro) (SEQ ID NO: 9)

(9a: Synthesis of Boc-Val-Gly-Lac-Pro (SEQ ID NO: 10)-OBzl)

HCl.H-Gly-Lac-Pro-OBzl (6.18 g, 16.7 mmol), NMM (1830 mL, 16.70 mmol), Boc-Val-OH (3.96 g, 18.20 mmol), DCC (3.78 g, 18.30 mmol), and HOBt.H$_2$O (0.50 g, 3.26 mmol) were used to cause a condensation reaction, whereby a yellow oil was obtained. The yield was 8.8 g (yield 99%). $^1$H NMR (DMSO-d$_6$, 300 MHz): 8.32 (1H, Gly NH); 7.37 (5H, OBzl C$_6$H$_5$—); 6.66 (1H, Val NH); 5.22 (1H, Lac αCH); 5.08 (2H, OBzl —CH$_2$—), 4.39 (1H, Pro αCH); 4.06 (1H, Val αCH); 3.77 (2H, Gly αCH$_2$); 3.53 (2H, Pro γCH$_2$); 2.20 (1H, Val βCH); 1.93 (2H, Pro γCH$_2$); 1.37 (9H, Boc t-Bu-); 1.27 (3H, Lac βCH$_3$); 0.87 (3H, Val γCH$_3$).

(Synthesis of 9b: HCl.H-Val-Gly-Lac-Pro (SEQ ID NO: 10)-OBzl)

To Boc-Val-Gly-Lac-Pro (SEQ ID NO: 10)-OBzl (2.35 g, 4.40 mmol) in THF solution, 4 M HCl/dioxane (11 mL) was added to deprotect an amino terminal. A colorless solid was obtained. The yield was 1.9 g (yield 92%). $^1$H NMR (DMSO-d$_6$, 300 MHz): 8.90 (1H, Gly NH); 8.17 (2H, Val NH$^{3+}$—); 7.35 (5H, OBzl C$_6$H$_5$—); 5.25 (Lac αCH); 5.09 (2H, OBzl —CH$_2$—); 4.37 (1H, Pro αCH); 4.17 (1H, Val αCH); 3.89 (Gly αCH$_2$); 3.48 (2H, Pro γCH$_2$); 2.20 (1H, Val βCH); 1.91 (2H, Pro γCH$_2$); 1.39 (3H, Lac βCH$_3$); 0.97 (6H, Val γCH$_3$).

(9c: Synthesis of Boc-Gly$^1$-Val$^2$-Gly$^3$-Lac$^4$-Pro$^5$ (SEQ ID NO: 9)-OBzl)

HCl.Val-Gly-Lac-Pro (SEQ ID NO: 10)-OBzl (3.55 g, 7.55 mmol), NMM (830 mL, 7.55 mmol), Boc-Gly-OH (1.47 g, 8.39 mmol), EDC.HCl (1.57 g, 8.19 mmol), and HOBt.H$_2$O (0.11 g, 0.718 mmol) were used to cause a condensation reaction, whereby a yellow oil was obtained. The yield was 7.7 g (yield 86%). $^1$H NMR (DMSO-d$_6$, 300 MHz): 8.48 (1H, Gly$^3$ NH); 7.60 (1H, Val NH); 7.33 (5H, OBzl C$_6$H$_5$—); 6.98 (1H, Gly$^1$ NH); 5.21 (1H, Lac αCH); 5.17 (2H, OBzl —CH$_2$—); 4.36 (1H, Pro αCH); 4.21 (1H, Val αCH); 3.73 (2H, Gly αCH$_2$); 3.55 (2H, Pro δCH$_2$); 2.19 (1H, Val βCH); 1.94 (2H, Pro γCH$_2$); 1.36 (9H, Boc tBu-); 1.25 (3H, Lac βCH$_3$); 0.87 (6H, Val γCH$_3$).

(9d: Synthesis of Boc-Gly$^1$-Val$^2$-Gly$^3$-Lac$^4$-Pro$^5$ (SEQ ID NO: 9)—OH)

Boc-Gly-Val-Gly-Lac-Pro (SEQ ID NO: 9)-OBzl (0.81 g, 1.37 mmol) was put in a 300-mL eggplant flask and dissolved by adding methanol. Then, two microspatulas of Pd-C powder were added thereto. A device was assembled and the 300-mL eggplant flask was filled with hydrogen gas and then stirring was started, followed by a catalytic reduction, After 5 hours, the completion of the reaction was confirmed with TLC. The Pd-C powder was removed and the filtrate was concentrated. After that, methanol and moisture were distilled off sufficiently by benzene azeotropy. Hexane following ethyl acetate was added to the residue, and the resultant was collected by filtration and dried under reduced pressure, whereby a colorless crystal was obtained. The yield was 0.5 g (yield 73%). $^1$H NMR (DMSO-d$_6$, 500 MHz): 8.51 (1H, Gly$^3$ NH); 7.67, 7.65 (1H, Val NH, two signals derived from structural isomerism); 7.00 (1H, Gly$^1$ NH); 5.21 (1H, Lac αCH); 4.20 (1H, Pro αCH); 3.98 (1H, Val αCH); 3.77 (2H, Gly αCH$_2$); 3.56 (2H, Pro δCH$_2$); 2.15 (1H, Val βCH); 1.80 (2H, Pro γCH$_2$); 1.35 (9H, Boc tBu-); 1.29 (3H, Lac βCH$_3$); 0.85 (6H, Val γCH$_3$).

(9e: Synthesis of Boc-Gly$^1$-Val$^2$-Gly$^3$-Lac$^4$-Pro$^5$ (SEQ ID NO: 9)-OSu)

Boc-Gly-Val-Gly-Lac-Pro (SEQ ID NO: 9)—OH (0.80 g, 1.60 mmol), HOSu (0.19 g, 1.65 mmol), DCC (0.39 g, 1.89 mmol) were used to a cause a condensation reaction in distilled THF, whereby a colorless crystal was obtained. The yield was 0.8 g (yield 85%). $^1$H NMR (DMSO-d$_6$, 500 MHz): 8.51 (1H, Gly$^3$ NH); 7.66, 7.63 (1H, Val NH, two signals derived from structural isomerism); 7.00 (1H, Gly$^1$ NH); 5.26 (1H, Lac αCH); 4.72 (1H, Pro αCH); 4.23 (1H, Val αCH); 3.77 (2H, Gly αCH$_2$); 3.56 (2H, Pro δCH$_2$); 2.79 (1H, Val βCH); 1.80 (2H, Pro γCH$_2$); 1.35 (9H, Boc tBu-); 1.29 (3H, Lac βCH$_3$); 0.85 (6H, Val γCH$_3$).

(9f: Synthesis of HCl.H-Gly$^1$-Val$^2$-Gly$^3$-Lac$^4$-Pro$^5$ (SEQ ID NO: 9)-OSu)

Boc-Gly-Val-Gly-Lac-Pro (SEQ ID NO: 9)-OSu (0.81 g, 1.35 mmol) in distilled chloroform solution was deprotected at the amino terminal. A colorless solid was obtained. The yield was 726 mg (yield: almost quantitative). $^1$H NMR (DMSO-d$_6$, 300 MHz): 8.61 (1H, Gly$^3$ NH); 8.52, 8.45 (1H, Val NH); 8.07 (1H, Gly$^1$ NH$^{3+}$—); 5.24 (1H, Lac αCH); 4.74 (1H, Pro αCH); 4.26 (1H, Val αCH); 3.77 (2H, Gly αCH$_2$); 3.62 (2H, Pro δCH$_2$); 2.04 (3H, Val βCH, Pro γCH$_2$); 1.34 (3H, Lac βCH$_3$); 0.92 (6H, Val γCH$_3$).

(9g: Synthesis of poly(Gly-Val-Gly-Lac-Pro) (SEQ ID NO: 9))

HCl.H-Gly-Val-Gly-Lac-Pro (SEQ ID NO: 9)-OSu (1.38 g, 2.58 mmol) was put in a 25-mL vial and dissolved by adding 1.2 mL of distilled DMF. Triethylamine (358 mM, 2.58 mmol) was added thereto, followed by stirring at around 35° C. for about 3 weeks. After 3 weeks, a reaction system was concentrated under reduced pressure, and acetonitrile was dropped slowly. A colorless powder was precipitated and collected by filtration. The powder was confirmed to be an objective product from $^1$H NMR measurement. An almost colorless objective solid was obtained. The yield was 673 mg (yield 65%). $^1$H NMR (DMSO-$d_6$, 300 MHz): 8.70 (1H, Gly$^3$ NH); 8.16 (1H, Gly$^1$ NH); 7.67, 7.63 (1H, Val NH); 5.25 (1H, Lac αCH); 4.20 (1H, Pro αCH); 3.68 (1H, Val αCH); 3.60 (2H, Gly αCH$_2$); 2.0 (5H, Val βCH, Pro γCH$_2$, Pro δCH$_2$); 1.33 (3H, Lac βCH$_3$); 0.88 (6H, Val γCH$_3$).

Example 10

(10) Mass Spectrometry by MALDI-TOF Method

Figure 7:
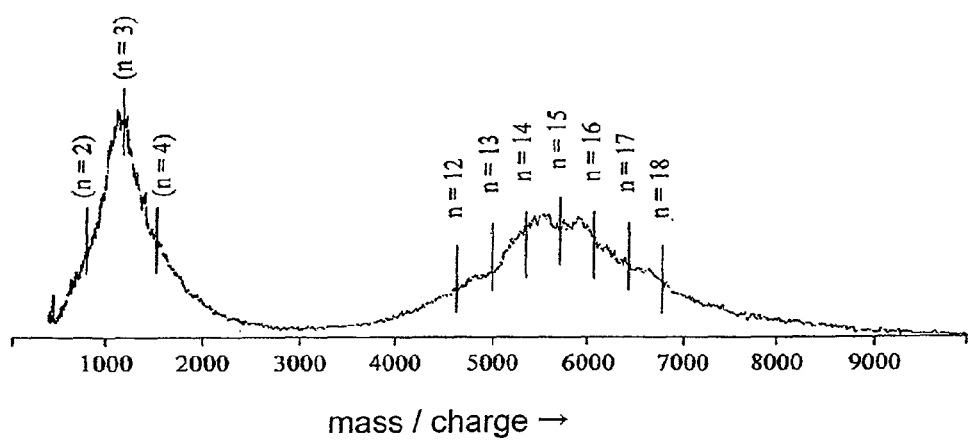
FIG. 7 illustrates a spectrum obtained by measuring poly(Gly-Val-Gly-Lac-Pro) (SEQ ID NO: 9) which is one embodiment of the present invention by MALDI-TOF mass spectrometry.

A MALDI-spectrum of the polymer compound obtained in Example 9 was measured. With the spectrum, the molecular weight of the polymer compound synthesized by the polymerization reaction can be confirmed. Here, an example of poly(Gly-Val-Gly-Lac-Pro) (SEQ ID NO: 9) is shown in FIG. 7. As a result, in poly(Gly-Val-Gly-Lac-Pro) (SEQ ID NO: 9) (mass of monomer unit=382.41), a strong signal was observed in a region of 12 mer to 18 mer. A signal in a low-molecular-weight region corresponds to an apparent dimer to tetramer. However, it was considered that a polyvalent ion of a high-molecular-weight product was actually observed.

Example 11

(11) Circular Dichroism Spectrum

Figure 8:
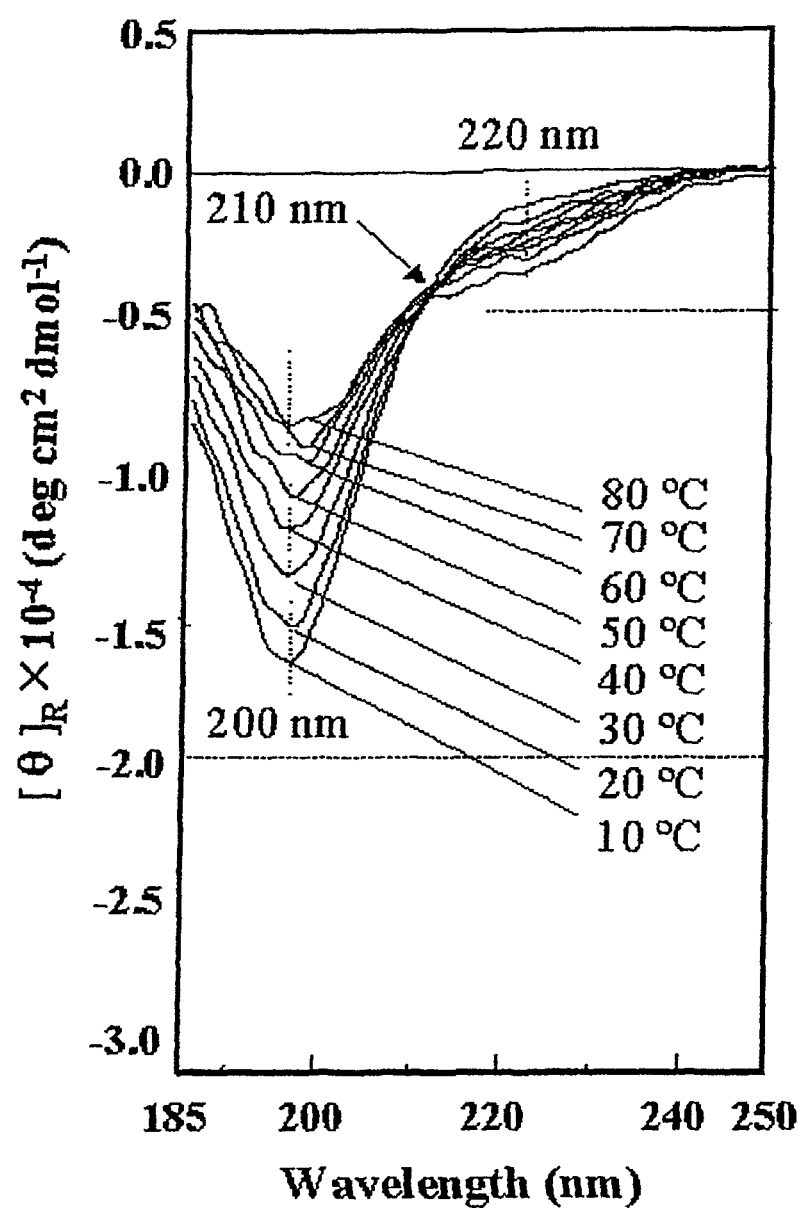
FIG. 8 illustrates circular dichroism spectra depending on temperature change. Measurement was performed according to the following procedure: an aqueous solution of poly(Gly-Val-Gly-Lac-Pro) (SEQ ID NO: 9) (0.1 mg/mL) which is one embodiment of the present invention was put in a 1-mm-thick quartz cell for absorption spectra; the temperature was increased by every 10° C. between 10° C. and 70° C.; and the spectrum was measured when the temperature equilibrated at each temperature.

A circular dichroism spectrum depending on the temperature of the polymer compound obtained in Example 9 was measured. From the spectrum, different information from the change in temperature responsiveness obtained by visual observation can be obtained. For example, a information about a solution structure can be obtained. Here, the example of poly(Gly-Val-Gly-Lac-Pro) (SEQ ID NO: 9) is shown in FIG. 8. As a result, spectrum was changed while indicating circular dichroism point at 210 nm. There is no aggregation because the sample is a dilute aqueous solution (0.1 mg/mL). With the increase in the temperature, the negative band recognized at 200 nm was confirmed to decrease.

Example 12

(12) Observation of Temperature Responsiveness by Apparent Absorbance

Figure 9:
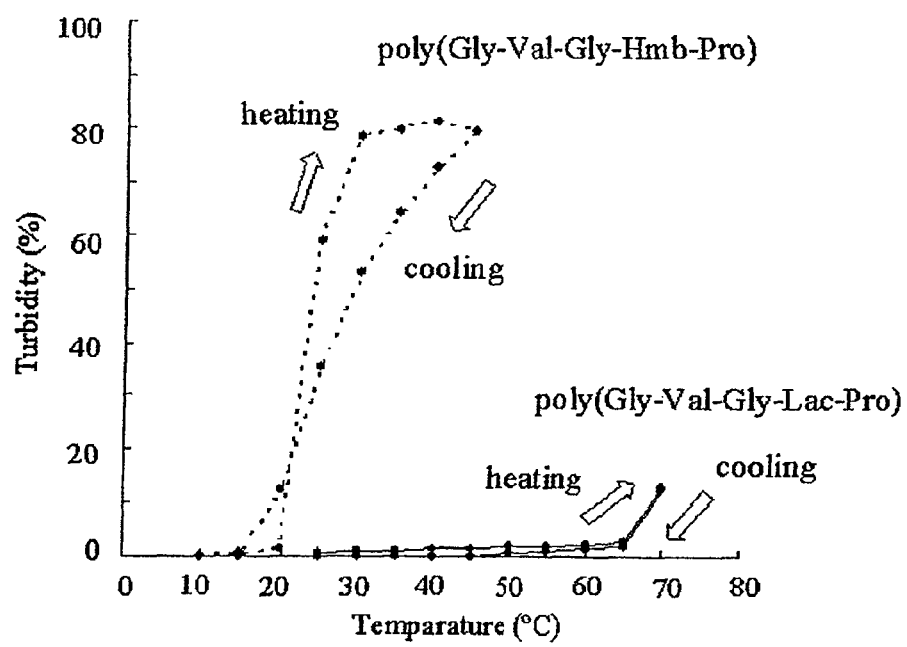
FIG. 9 illustrates a graph obtained by the following procedure: an aqueous solution of poly(Gly-Val-Gly-Lac-Pro) (SEQ ID NO: 9) (10 mg/mL) which is one embodiment of the present invention was put in a 1-mm-thick quartz cell for absorption spectra; the temperature was increased at a rate of 1° C./5 minutes between 20° C. and 70° C. and then decreased; transmittance (%) was measured with respect to a light of 350 nm at each temperature in a 1° C. interval; and a turbidity (%) obtained by subtracting the transmittance (%) from 100 was plotted. In addition, as a comparative example, a plot of an aqueous solution (10 mg/mL) of poly(Gly-Val-Gly-Hmb-Pro) was shown.

The change in temperature responsiveness of the polymer obtained in Examples 9 due to heating an aqueous solution of the polymer was observed by apparent absorbance. The wavelength for observation was 350 nm. The wavelength corresponds to the phenomenon of light scattering, i.e. white turbidity, by visual observation. Here, the data are shown in FIG. 9 to compare with poly(Gly-Val-Gly-Hmb-Pro) (SEQ ID NO: 2) (Hmb=2-hydroxy-3-methylbutanoic acid). The ordinate axes each represent turbidity converted from the transmittance. From the figure, the difference in the phase transition temperature due to difference in hydroxycarboxylic acid groups can be clarified. That is, in the case where the temperature-increase rate and the temperature-decrease rate were 1° C./5 minutes, poly(Gly-Val-Gly-Hmb-Pro) (SEQ ID NO: 2) aggregated at 20 to 30° C. On the other hand, in the same condition, the aggregation temperature of poly(Gly-Val-Gly-Lac-Pro) (SEQ ID NO: 9) was confirmed to be 70° C. or higher. This is because the phase transition temperature decreased with higher hydrophobicity.

Figure 10:
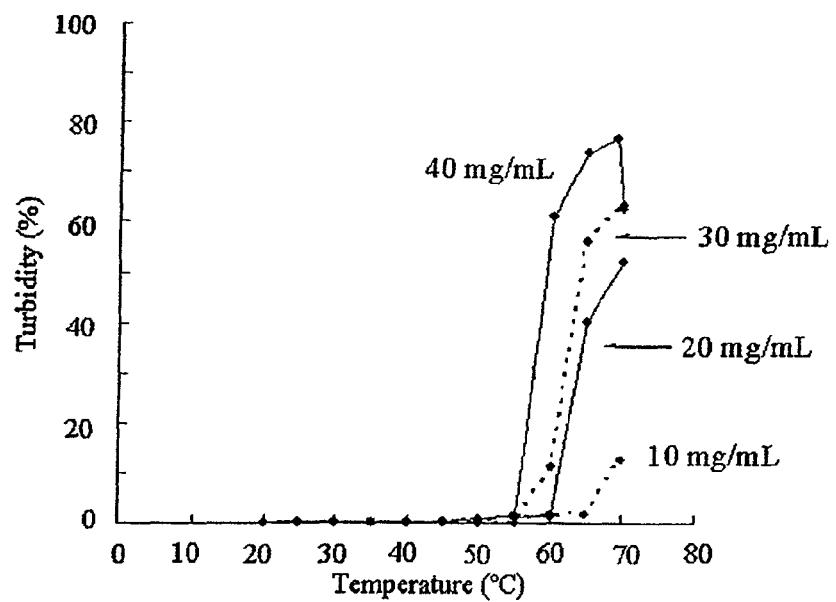
FIG. 10 illustrates a graph obtained by the following procedure: an aqueous solution of poly(Gly-Val-Gly-Lac-Pro) (SEQ ID NO: 9) which is one embodiment of the present invention with different concentrations (10, 20, 30, and 40 mg/mL) was put in a 1-mm-thick quartz cell for absorption spectra; the temperature was increased at a rate of 1° C./5 minutes between 20° C. and 70° C. and then decreased; transmittance (%) was measured with respect to a light of 350 nm at each temperature in a 1° C. interval; and a turbidity (%) obtained by subtracting the transmittance (%) from 100 was plotted.

As shown in FIG. 10, with the increase in the concentration of the aqueous solution of poly(Gly-Val-Gly-Lac-Pro) (SEQ ID NO: 9), aggregation was observed at 70° C. or lower. In addition, the phase transition phenomenon was reversible (FIG. 11), and in the range of 10 to 40 mg/mL, the aggregation temperature was confirmed to decrease with the increase in the concentration (FIG. 10).

INDUSTRIAL APPLICABILITY

The depsipeptide compound or the polymer thereof of the present invention can be used as a material for the temperature responsive depsipeptide or a temperature responsive composition containing the material. The temperature responsive material and composition of the present invention can be applied to constitution of a composition which is degraded and absorbed in an organism, a composition which is degraded and absorbed under an environment such as soil, a cell adhesion agent, a drug carrier, a wound dressing material, an artificial muscle, a microcapsule, a biomachine, a biosensor, a separation membrane, a test kit, or the like. Those can be easily developed based on the research involved by the inventors of the present invention (for example, Yoshida et al., Advanced Materials, 1997, Vol. 9, page 757; Hiroki et al., Journal of Polymer Science, 1998, Vol. 36, page 1495; JP 07-233194 A; Yoshida et al., Drug Design and Delivery, 1991, Vol. 7, page 159; Mashita et al., The KITAKANTO Medical Journal, 1991, Vol. 41, page 311).

What is claimed is:

1. A compound, which is represented by the following general formula (I)

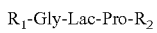  (I):

where

-Gly-Lac-Pro- represents a structure represented by the following formula (II),

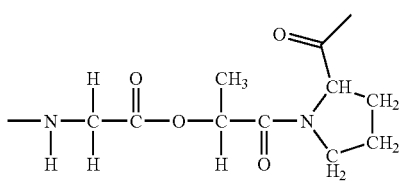  (II)

$R_1$ represents a hydrogen atom, an amino acid, a polypeptide, or a hydroxycarboxylic acid which are linked through an amide bond, and $R_2$ represents a hydroxyl group, an amino acid, or a polypeptide which are linked through an amide bond, or a hydroxycarboxylic acid which is linked through an ester bond.

2. The compound according to claim 1, wherein the general formula (I) is $X_1$-$X_2$-Gly-Lac-Pro (SEQ ID NO: 6) where $X_1$ and $X_2$ represent an α-amino acid residue.

3. A polymer, which is obtained by polymerizing the compound according to claim 1 or 2.

4. The compound according to claim 1 or 2, wherein a sugar chain sequence, a protein, a polysaccharide, a metal complex, a polymer carrier, a gel, a film, a latex particle, a metal fine particle, an inorganic fine particle, a glass plate, or a plastic plate is linked to a terminal of the compound.

5. A composition, which is obtained by mixing the compound according to claim 1 or 2 with water, a buffer solution, a salt solution, or a water-containing organic solvent, wherein the composition forms a solvation state, a gel state, a suspension, a uniform solution, or a phase separation state.

6. The composition according to claim 5, which releases water molecules by heating and incorporates water molecules by cooling.

7. A temperature responsive composition, comprising the compound according to claim 1 or 2.

8. The polymer according to claim 3, wherein a sugar chain sequence, a protein, a polysaccharide, a metal complex, a polymer carrier, a gel, a film, a latex particle, a metal fine particle, an inorganic fine particle, a glass plate, or a plastic plate is linked to a terminal of the polymer.

9. A composition, which is obtained by mixing the polymer according to claim 3 with water, a buffer solution, a salt solution, or a water-containing organic solvent, wherein the composition forms a solvation state, a gel state, a suspension, a uniform solution, or a phase separation state.

10. The composition according to claim 9, which releases water molecules by heating and incorporates water molecules by cooling.

11. A temperature responsive composition, comprising the polymer according to claim 3.

* * * * *